(12) United States Patent
Barthe et al.

(10) Patent No.: US 7,491,171 B2
(45) Date of Patent: Feb. 17, 2009

(54) METHOD AND SYSTEM FOR TREATING ACNE AND SEBACEOUS GLANDS

(75) Inventors: Peter G. Barthe, Phoenix, AZ (US); Michael H. Slayton, Tempe, AZ (US); Inder Raj S. Makin, Mesa, AZ (US)

(73) Assignee: Guided Therapy Systems, L.L.C., Mesa, AZ (US)

( * ) Notice: Subject to any disclaimer, the term of this patent is extended or adjusted under 35 U.S.C. 154(b) by 228 days.

(21) Appl. No.: 11/163,177

(22) Filed: Oct. 7, 2005

(65) Prior Publication Data

US 2006/0089632 A1    Apr. 27, 2006

Related U.S. Application Data

(60) Provisional application No. 60/617,203, filed on Oct. 7, 2004.

(51) Int. Cl.
*A61B 8/00* (2006.01)
(52) U.S. Cl. .............................. 600/439; 600/437; 601/2
(58) Field of Classification Search ................. 600/439, 600/437, 440; 601/2–4; 607/88; 606/9, 606/10; 128/399; 604/22
See application file for complete search history.

(56) References Cited

U.S. PATENT DOCUMENTS

| | | |
|---|---|---|
| 4,372,296 A | 2/1983 | Fahim |
| 4,528,979 A | 7/1985 | Marchenko |
| 4,858,613 A | 8/1989 | Fry |
| 4,951,653 A | 8/1990 | Fry |
| 4,955,365 A | 9/1990 | Fry |
| 5,054,470 A | 10/1991 | Fry |
| 5,115,814 A | 5/1992 | Griffith et al. |
| 5,117,832 A | 6/1992 | Sanghvi |
| 5,150,711 A | 9/1992 | Dory |
| 5,230,334 A | 7/1993 | Klopotek |
| 5,524,620 A | 6/1996 | Rosenschein et al. |
| 5,601,526 A | 2/1997 | Chapelon |

(Continued)

FOREIGN PATENT DOCUMENTS

EP    1234566    8/2002

(Continued)

*Primary Examiner*—Eric F Winakur
*Assistant Examiner*—Lawrence N Laryea
(74) *Attorney, Agent, or Firm*—Snell & Wilmer L.L.P.

(57) ABSTRACT

A method and system for ultrasound treatment of acne and sebaceous glands are provided. An exemplary method and system are configured for targeted treatment of sebaceous glands in various manners, such as through use of therapy only, therapy and monitoring, imaging and therapy, or therapy, imaging, and monitoring, and/or through use of focused, unfocused, or defocused ultrasound at various spatial and temporal energy settings. An exemplary method and system can be configured to produce regions of heating and damage by destroying the function of sebaceous glands within a user-specified treatment layer depth associated with the glands to be treated. In addition, an exemplary method and system can be configured to produce regions of heating and damage within the treatment layer in spatially defined patterns, rather than heating and destroying the entire volume of the target layer of tissue. Further, an exemplary method and system can be configured to specifically aim such regions of heating and damage within the treatment layer, to occur at the same location as the secretory portion of sebaceous glands.

25 Claims, 23 Drawing Sheets

U.S. PATENT DOCUMENTS

| | | | |
|---|---|---|---|
| 5,676,692 A | 10/1997 | Sanghvi | |
| 5,690,608 A | 11/1997 | Watanabe | |
| 5,755,753 A | 5/1998 | Knowlton | |
| 5,762,066 A | 6/1998 | Law | |
| 5,873,902 A | 2/1999 | Sanghvi | |
| 5,938,612 A | 8/1999 | Kline-Schoder | |
| 6,090,054 A | 7/2000 | Tagishi | |
| 6,093,883 A | 7/2000 | Sanghvi | |
| 6,113,559 A | 9/2000 | Klopotek | |
| 6,176,840 B1 | 1/2001 | Nishimura | |
| 6,183,426 B1 | 2/2001 | Akisada | |
| 6,183,773 B1 * | 2/2001 | Anderson | 424/450 |
| 6,241,753 B1 | 6/2001 | Knowlton | |
| 6,315,741 B1 | 11/2001 | Martin et al. | |
| 6,325,769 B1 | 12/2001 | Klopotek | |
| 6,350,276 B1 | 2/2002 | Knowlton | |
| 6,361,531 B1 | 3/2002 | Hissong | |
| 6,377,855 B1 | 4/2002 | Knowlton | |
| 6,381,498 B1 | 4/2002 | Knowlton | |
| 6,413,254 B1 | 7/2002 | Hissong | |
| 6,425,912 B1 | 7/2002 | Knowlton | |
| 6,440,121 B1 | 8/2002 | Weber | |
| 6,500,121 B1 * | 12/2002 | Slayton et al. | 600/439 |
| 6,511,428 B1 | 1/2003 | Azuma et al. | |
| 6,514,244 B2 | 2/2003 | Pope | |
| 6,595,934 B1 * | 7/2003 | Hissong et al. | 601/3 |
| 6,607,498 B2 | 8/2003 | Eshel | |
| 6,623,430 B1 | 9/2003 | Slayton et al. | |
| 6,692,450 B1 | 2/2004 | Coleman | |
| 6,932,771 B2 | 8/2005 | Whitmore et al. | |
| 6,936,046 B2 | 8/2005 | Hissong | |
| 6,958,043 B2 | 10/2005 | Hissong | |
| 6,976,492 B2 | 12/2005 | Ingle et al. | |
| 7,020,528 B2 * | 3/2006 | Neev | 607/100 |
| 7,063,666 B2 | 6/2006 | Weng et al. | |
| 7,179,238 B2 | 2/2007 | Hissong | |
| 7,258,674 B2 | 8/2007 | Cribbs et al. | |
| 7,347,855 B2 | 3/2008 | Eshel et al. | |
| 2001/0009997 A1 | 7/2001 | Pope | |
| 2002/0040199 A1 | 4/2002 | Klopotek | |
| 2002/0055702 A1 | 5/2002 | Atala et al. | |
| 2002/0161357 A1 | 10/2002 | Anderson et al. | |
| 2002/0169442 A1 * | 11/2002 | Neev | 606/9 |
| 2003/0050678 A1 * | 3/2003 | Sierra et al. | 607/89 |
| 2003/0065313 A1 | 4/2003 | Koop | |
| 2003/0083536 A1 | 5/2003 | Eshel | |
| 2003/0176790 A1 | 9/2003 | Slayton et al. | |
| 2003/0191396 A1 | 10/2003 | Sanghvi | |
| 2003/0216795 A1 * | 11/2003 | Harth et al. | 607/88 |
| 2003/0220536 A1 | 11/2003 | Hissong | |
| 2003/0220585 A1 | 11/2003 | Hissong | |
| 2004/0015106 A1 | 1/2004 | Coleman | |
| 2004/0030227 A1 | 2/2004 | Littrup et al. | |
| 2004/0039312 A1 | 2/2004 | Hillstead | |
| 2004/0059266 A1 | 3/2004 | Fry | |
| 2004/0206365 A1 | 10/2004 | Knowlton | |
| 2005/0055073 A1 | 3/2005 | Weber | |
| 2005/0154332 A1 * | 7/2005 | Zanelli et al. | 601/2 |
| 2005/0261584 A1 | 11/2005 | Eshel | |
| 2005/0267454 A1 | 12/2005 | Hissong | |
| 2006/0074313 A1 | 4/2006 | Slayton et al. | |
| 2006/0074314 A1 | 4/2006 | Slayton et al. | |
| 2006/0079868 A1 | 4/2006 | Makin et al. | |
| 2006/0089688 A1 | 4/2006 | Panescu | |
| 2006/0111744 A1 | 5/2006 | Makin et al. | |
| 2006/0116671 A1 | 6/2006 | Slayton et al. | |
| 2006/0122508 A1 | 6/2006 | Slayton et al. | |
| 2006/0122509 A1 | 6/2006 | Desilets | |
| 2006/0241440 A1 | 10/2006 | Eshel | |
| 2006/0241442 A1 | 10/2006 | Barthe et al. | |
| 2007/0032784 A1 | 2/2007 | Gliklich et al. | |
| 2007/0055156 A1 | 3/2007 | Desilets | |

FOREIGN PATENT DOCUMENTS

| | | |
|---|---|---|
| EP | 1262160 | 12/2002 |
| JP | 3123559 | 5/1991 |
| JP | 4089058 | 3/1992 |
| JP | 7080087 | 3/1995 |
| JP | 7222782 | 8/1995 |
| WO | WO0015300 | 3/2000 |
| WO | WO0021612 | 4/2000 |
| WO | WO0128623 | 4/2001 |
| WO | WO0182778 | 11/2001 |
| WO | WO0187161 | 11/2001 |
| WO | WO0209813 | 2/2002 |
| WO | WO03070105 | 8/2003 |
| WO | WO03077833 | 9/2003 |

* cited by examiner

METHOD AND SYSTEM FOR TREATING ACNE AND SEBACEOUS GLANDS

CROSS-REFERENCE TO RELATED APPLICATIONS

This Application claims priority to and benefit of U.S. Provisional Application No. 60/617,203, entitled "Method and System for Treating Acne and Sebaceous Glands", and filed on Oct. 7, 2004.

FIELD OF INVENTION

The present invention relates to ultrasound treatment systems, and in particular to a method and system for treating acne and sebaceous glands.

BACKGROUND OF INVENTION

Acne vulgaris is the most common skin disorder. Acne causes temporary and permanent disfigurement. Acne typically appears on the face, back and/or chest at the onset of adrenarchy, i.e. when sex hormone activity increases in both boys and girls near puberty. Acne is a disorder of hair follicles, in which a plug forms within the outflow tract of the hair follicle. Sebum, an oily product of sebaceous glands attached to each hair follicle, and cellular debris builds in the plug. Inflammation and often rupture of the hair follicles ensues, leading to gross inflammation, pus (a "whitehead"), pain, bleeding, and/or eventually scarring. If the acne lesion consists of an accumulated unruptured plug within the hair follicle, a "blackhead" forms. If the follicle ruptures superficially, a small pustule forms that often heals after a few weeks without scarring. If the follicle ruptures within the mid or deep dermis, a painful cystic abscess forms. Cystic acne usually heals with permanent and disfiguring scars.

The exact pathophysiology of acne is complex and is not fully understood. However, several basic elements are necessary to produce an acne lesion, and acne therapies are based on attacking one or more of these basic elements. First, an active sebaceous gland is necessary. The most potent treatments for acne are oral retinoids such as retinoic acid (Accutane), which inhibit sebaceous gland function. Sebaceous gland activity is driven by androgen and other sex steroid hormones. Women often experience cycle-dependent acne that may respond to treatment with birth control pills containing low amounts of progestins. Second, a plug must form in the outflow tract of the follicle, called the infundibulum. Bacteria, particularly *Proprionobacteria acnes* (*P acnes*) that digest sebum and follicular debris, contribute to plugging. Topical retinoids, mild acids and benzoyl peroxide are used as treatments to decrease follicular plugging. Antibiotics effective against *P acnes* are given either topically or orally; the prevalence of antibiotic-resistant *P acnes* is increasing. Third, inflammation is part of the process that breaks down the wall of a follicle containing plugs, leading to rupture of the follicle with release of irritating materials into the skin, abscess formation, and scarring. Anti-inflammatory agents including some antibiotics are helpful in treating acne.

The most potent treatment for acne at present is oral retinoid therapy. Unfortunately, this is a toxic and teratogenic treatment. Unplanned pregnancies in women taking Accutane lead to a high rate of fetal malformations. An aggressive program to prevent this in the US was implemented, but has failed to prevent the problem. Systemic retinoid treatment also causes major side effects including extreme dryness during treatment, risk of hepatitis, bone changes, mood changes, and others. The high effectiveness and high toxicity of oral retinoids for treatment of cystic acne strongly suggests that an alternative treatment that targets sebaceous glands is needed.

SUMMARY OF INVENTION

A method and system for ultrasound treatment of acne and sebaceous glands are provided. An exemplary method and system are configured for targeted treatment of sebaceous glands in various manners, such as through use of therapy only, therapy and monitoring, imaging and therapy, or therapy, imaging, and monitoring. Targeted therapy of sebaceous glands can be provided through use of focused, unfocused, or defocused ultrasound at various spatial and temporal energy settings.

An exemplary method and system are configured to produce regions of heating and damage in various manners. For example, an exemplary method and system can be configured to produce regions of heating and damage by destroying the function of sebaceous glands within a user-specified treatment layer depth associated with the glands to be treated. In addition, an exemplary method and system can be configured to produce regions of heating and damage within the treatment layer in spatially defined patterns, rather than heating and destroying the entire volume of the target layer of tissue. Further, an exemplary method and system can be configured to specifically aim such regions of heating and damage within the treatment layer, to occur at the same location as the secretory portion of sebaceous glands.

In accordance with an exemplary embodiment, an exemplary treatment system comprises a control system, an imaging/therapy probe, and display system. The imaging/therapy probe can comprise various probe and/or transducer configurations. For example, the probe can be configured for a combined dual-mode imaging/therapy transducer, coupled or co-housed imaging/therapy transducers, a therapy probe, or simply a therapy probe and an imaging probe. The control system and display system can also comprise various configurations for controlling probe and system functionality, including for example a microprocessor with software and a plurality of input/output devices, a system for controlling electronic and/or mechanical scanning and/or multiplexing of transducers, a system for power delivery, systems for monitoring, systems for sensing the spatial position of the probe and/or transducers, and systems for handling user input and recording treatment results, among others.

In accordance with an exemplary embodiment, ultrasound imaging can be used for safety purposes, namely, to avoid injuring vital structures. In accordance with another exemplary embodiment, ultrasound imaging can be used to define the position of a sebaceous gland and/or the depth of sebaceous glands over a region of interest. Such glands can be seen lying along hair follicles and their image may be further enhanced via signal and image processing.

In accordance with an exemplary embodiment, ultrasound therapy via focused, unfocused, or defocused ultrasound, delivered via an array of foci or array of treatment zones, a locus of foci or locus treatment zones, a line focus or linear treatment zone, a surface or volume focus or surface or volume treatment zone, and/or diffraction patterns from single element, multiple elements, annular array, one-, two-, or three-dimensional arrays, broadband transducers, and/or combinations thereof, with or without lenses, acoustic components, mechanical and/or electronic focusing or defocusing are utilized to treat sebaceous glands at fixed and/or variable depth or dynamically controllable depths and positions.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a method and system for treating acne and sebaceous glands as described herein are merely indicative of exemplary applications for the invention. For example, the principles, features and methods discussed may be applied to any medical application. Further, various aspects of the present invention may be suitably applied to other applications.

Figure 1:
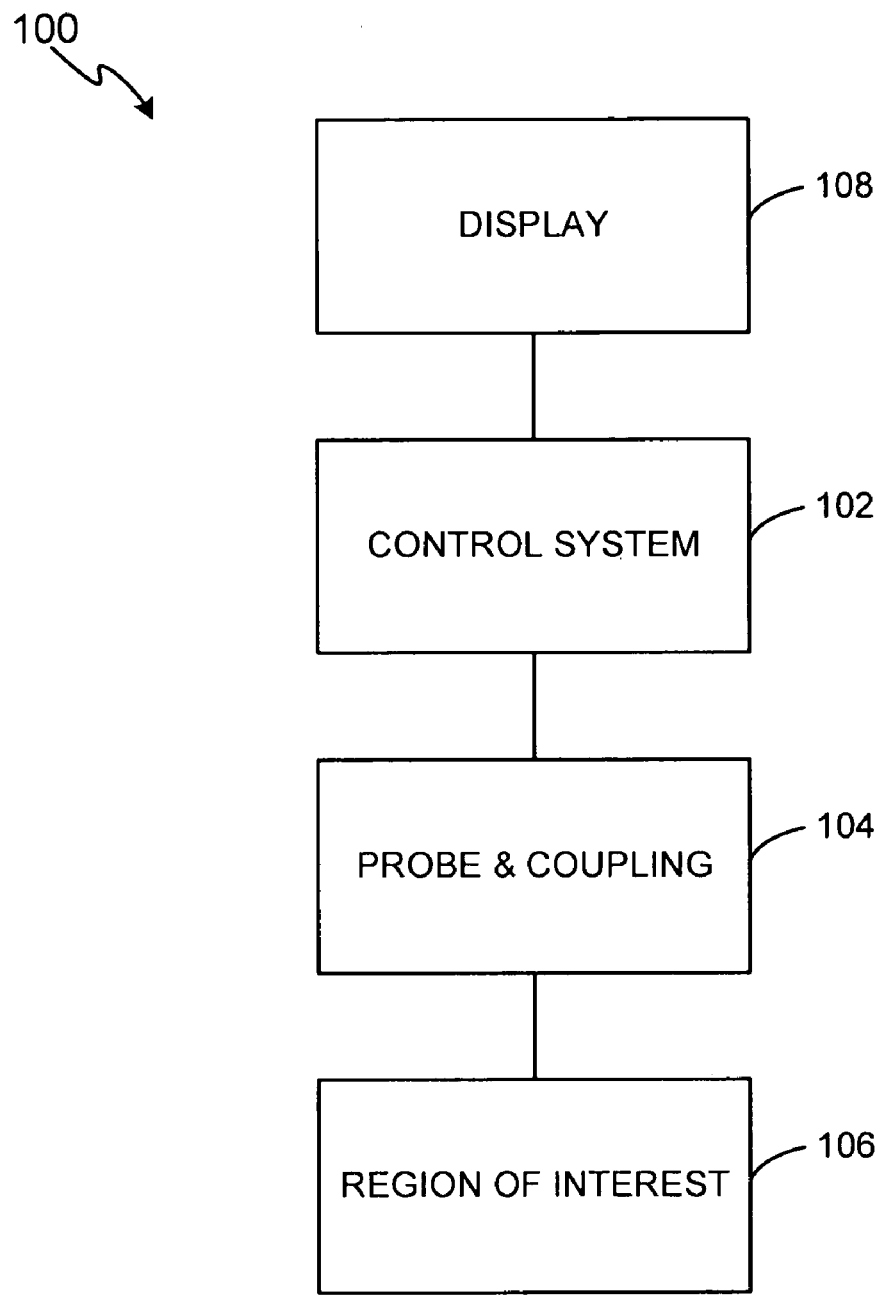
FIG. 1 illustrates a block diagram of a treatment system in accordance with an exemplary embodiment of the present invention.

In patients with acne it is desirable to temporarily or permanently destroy sebaceous glands. The depth at which these glands occur is approximately 1-7 mm, depending on skin thickness and body site. In accordance with various aspects of the present invention, a method and system for treating acne and sebaceous glands are provided. For example, in accordance with an exemplary embodiment, with reference to FIG. 1, an exemplary treatment system 100 configured to treat a region of interest (ROI) 106 comprises a control system 102, an imaging/therapy probe with acoustic coupling 104, and display system 108.

Control system 102 and display 108 can comprise various configurations for controlling functionality of probe 104 and system 100, including for example a microprocessor with software and a plurality of input/output and communication devices, a system for controlling electronic and/or mechanical scanning and/or multiplexing of transducers, a system for power delivery, systems for monitoring, systems for sensing the spatial position of the probe and/or temporal parameters of the transducers, and/or systems for handling user input and recording treatment input and results, among others. Imaging/therapy probe 104 can comprise various probe and/or transducer configurations. For example, probe 104 can be configured for a combined dual-mode imaging/therapy transducer, coupled or co-housed imaging/therapy transducers, a separate therapy probe and separate imaging probe, or a single therapy probe. In accordance with exemplary embodiments, imaging transducers may operate at frequencies from approximately 2 to 75 MHz or more, while therapy energy can be delivered at frequencies from approximately 2 to 50 MHz, with 2 MHz to 25 MHz being typical.

Figure 2A:
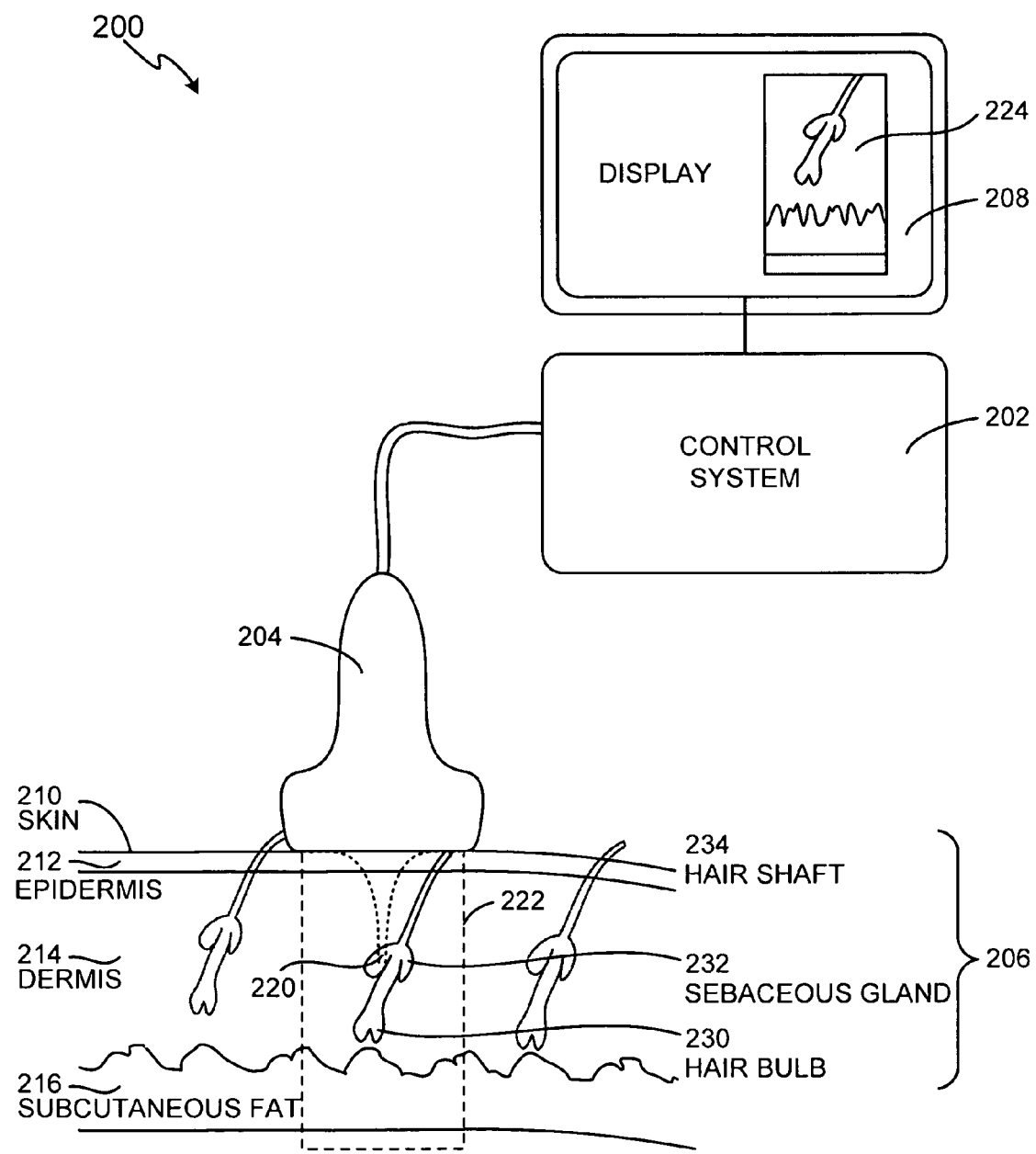
FIGS. 2A-2E illustrates schematic diagrams of ultrasound treatment systems configured to treat the sebaceous gland via direct targeting of heating and damage within the treatment layer in accordance with various exemplary embodiments of the present invention.

With reference to FIG. 2A, an exemplary treatment method and system are configured for initially imaging a region 222 within a region of interest 206 and displaying that region 224 on a display 208 to facilitate localization of the treatment area and surrounding structures, e.g., identification of sebaceous glands 232. After localization, delivery of ultrasound energy 220 at a depth, distribution, timing, and energy level to achieve the desired therapeutic effect of thermal ablation to treat a sebaceous gland 232 is provided. Before, during, and/or after therapy, i.e., before, during and/or after delivery of ultrasound energy, monitoring of the treatment area and surrounding structures can be conducted to further planning and assessing of the results and/or providing feedback to control system 202 and a system operator.

In accordance with an exemplary embodiment, localization can be facilitated through ultrasound imaging that can be used to define the position of a sebaceous gland and/or the depth of sebaceous glands over a region of interest. Such glands can be seen lying along hair follicles and their image may be further enhanced via signal and image processing. Ultrasound imaging can also be used for safety purposes, namely, to avoid injuring vital structures. In accordance with other exemplary embodiments, localization can also be accomplished without imaging region 222, but instead can be based on prior known depths of sebaceous glands or other target regions.

For ultrasound energy delivery, probe 204 and/or imaging/therapy transducers can be mechanically and/or electronically scanned, for example along direction 226, to place treatment zones over an extended area. A treatment depth 220 can be adjusted between a range of approximately 1 to 7 mm, and/or the greatest depth of sebaceous glands 232. Such delivery of energy can occur through a repeated "image and burn" technique, i.e., imaging of the targeted sebaceous gland and then applying ultrasound energy, or through a "carpet bomb" technique, i.e., applying ultrasound energy at known depths over an extended area without initial or ongoing imaging.

Figure 2B:
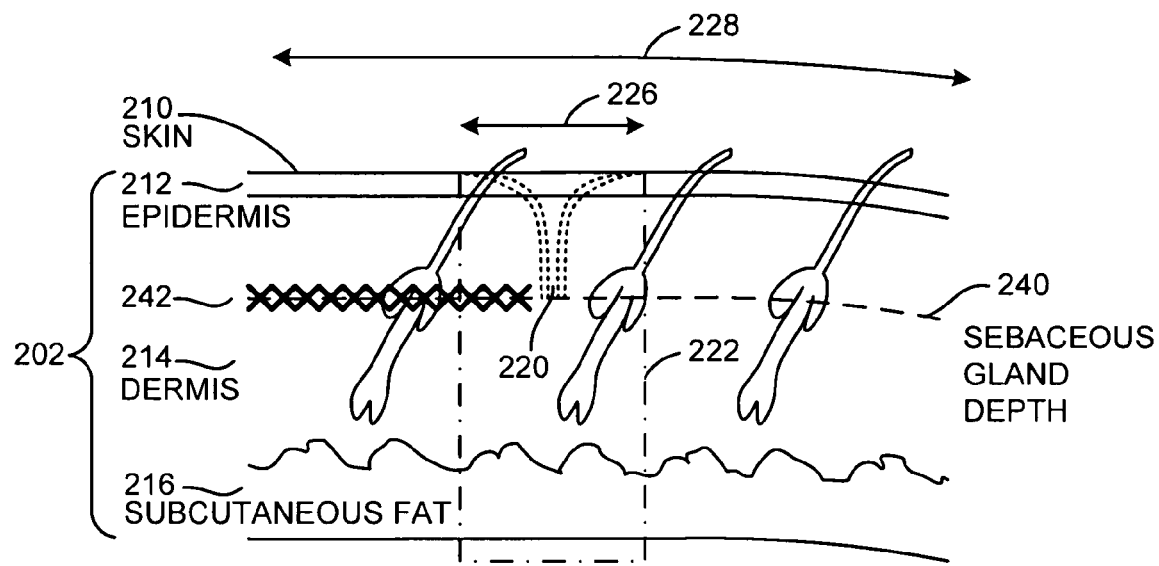

With reference to FIG. 2B, a treated zone 242 may extend over a line, plane, or surface, or over an extended zone across the sebaceous gland depth 240 that typically ranges from approximately 1 to 7 mm. Probe 204 can be mechanically and/or electronically scanned, for example directionally along 226, to extend treatment zone 242 over a large area. Probe 204 can be further scanned or moved along a longer directional line 228 to further enlarge treatment zone 242. For any treated zone 242, as treated zone 242 increases in depth within region of interest 206, the cross sectional area of treated zone 242 may increase in size from small to medium to large, i.e., at greater depths, the size of the treated lesion will increase. Furthermore a treated zone 242 can have a lesion shape expanding in cross section with depth, and/or be composed of the fusion of several smaller treatment zones. For example, a "cross-stitched" series of lesions, a wedge shaped series of lesions, or any suitably formed conformal lesions can be crated along treated zone 242.

The ultrasound beam from probe 204 can be spatially and/or temporally controlled by changing the spatial parameters of the transducer, such as the placement, distance, treatment depth and transducer structure, as well as by changing the temporal parameters of transducer, such as the frequency, drive amplitude, and timing, with such control handled via control system 202. Such spatial and temporal parameters can also be suitably monitored and/or utilized in open-loop and/or closed-loop feedback systems within treatment system 200. As a result of such spatial and/or temporal control, conformal lesions of various, specifically targeted, shapes, sizes and orientations can be configured along treatment zone 242.

Figure 2C:
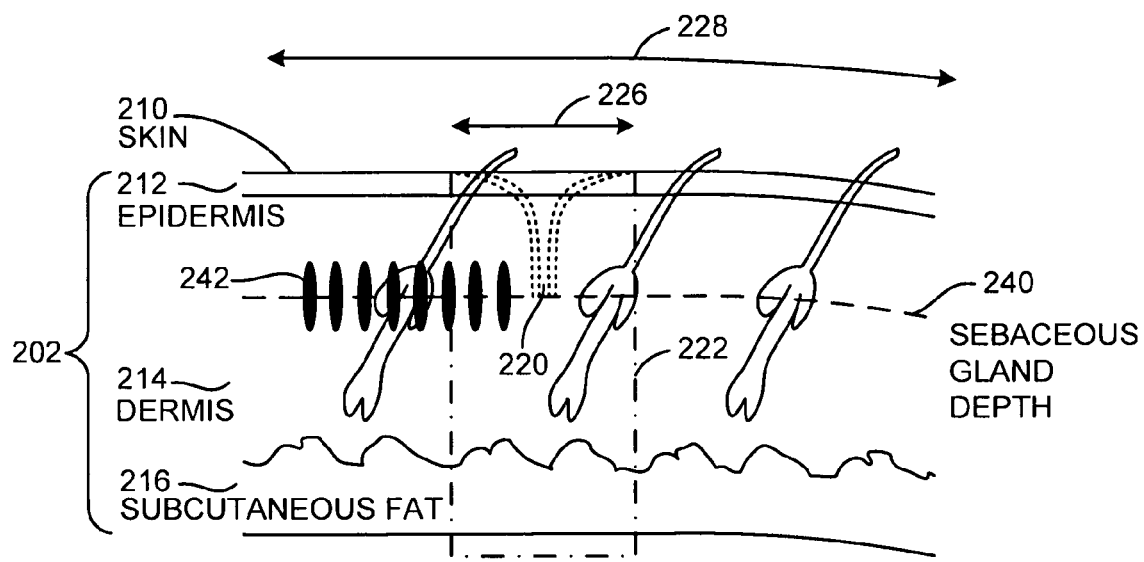

In accordance with an exemplary embodiment, with reference to FIG. 2C, one or more treated zones 242 can be configured to produce regions of heating and damage within the treatment layer in spatially defined patterns, such as a discrete locus of spaced treatment spots or two- or three- dimensional matrix of damage or destroyed tissue, e.g., a matrix of cross-stitched, ellipsoidal/cigar-shaped, wedge-shaped, mushroom-shaped or any other conformal lesions, rather than heating and destroying the entire volume of the target layer of tissue. In such a treatment where surrounding regions are spared of damage, the surrounding undamaged tissue aids rapid healing and recovery.

Figure 2D:
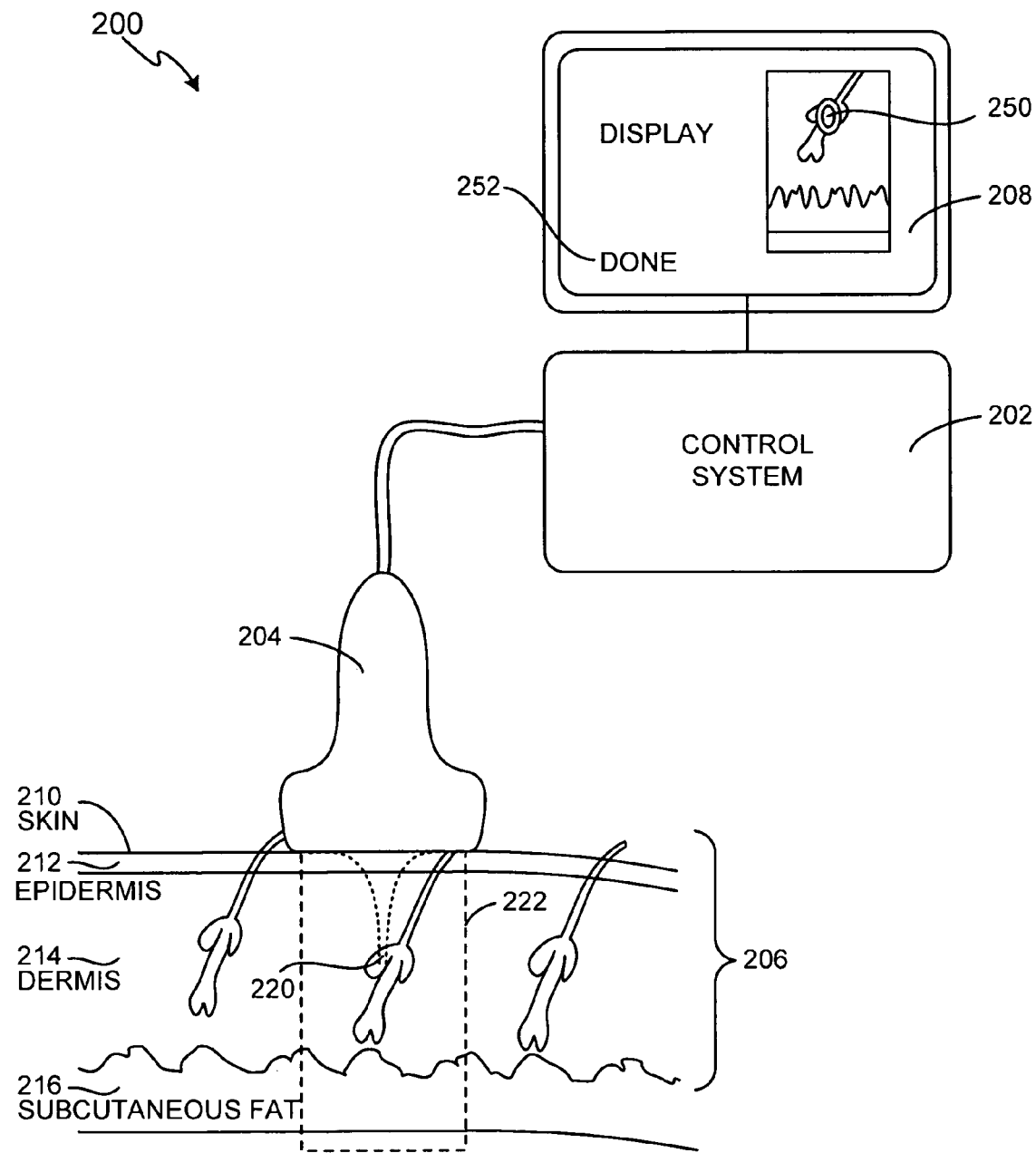

In accordance with another exemplary embodiment of the present invention, with reference to FIG. 2D, an exemplary monitoring method may comprise monitoring the temperature profile or other tissue parameters of the region of interest 206, such as attenuation, speed of sound, or mechanical properties such as stiffness and strain of the treatment region and suitably adjust the spatial and/or temporal characteristics and energy levels of the ultrasound therapy transducer of probe 204. The results of such monitoring techniques may be indicated on display 208 by means of one-, two-, or three-dimensional images of monitoring results 250, or may simply comprise a success or fail-type indicator 252, or combinations thereof. Additional treatment monitoring techniques may be based on one or more of temperature, video, profilometry, and/or stiffness or strain gauges or any other suitable sensing technique.

Figure 2E:
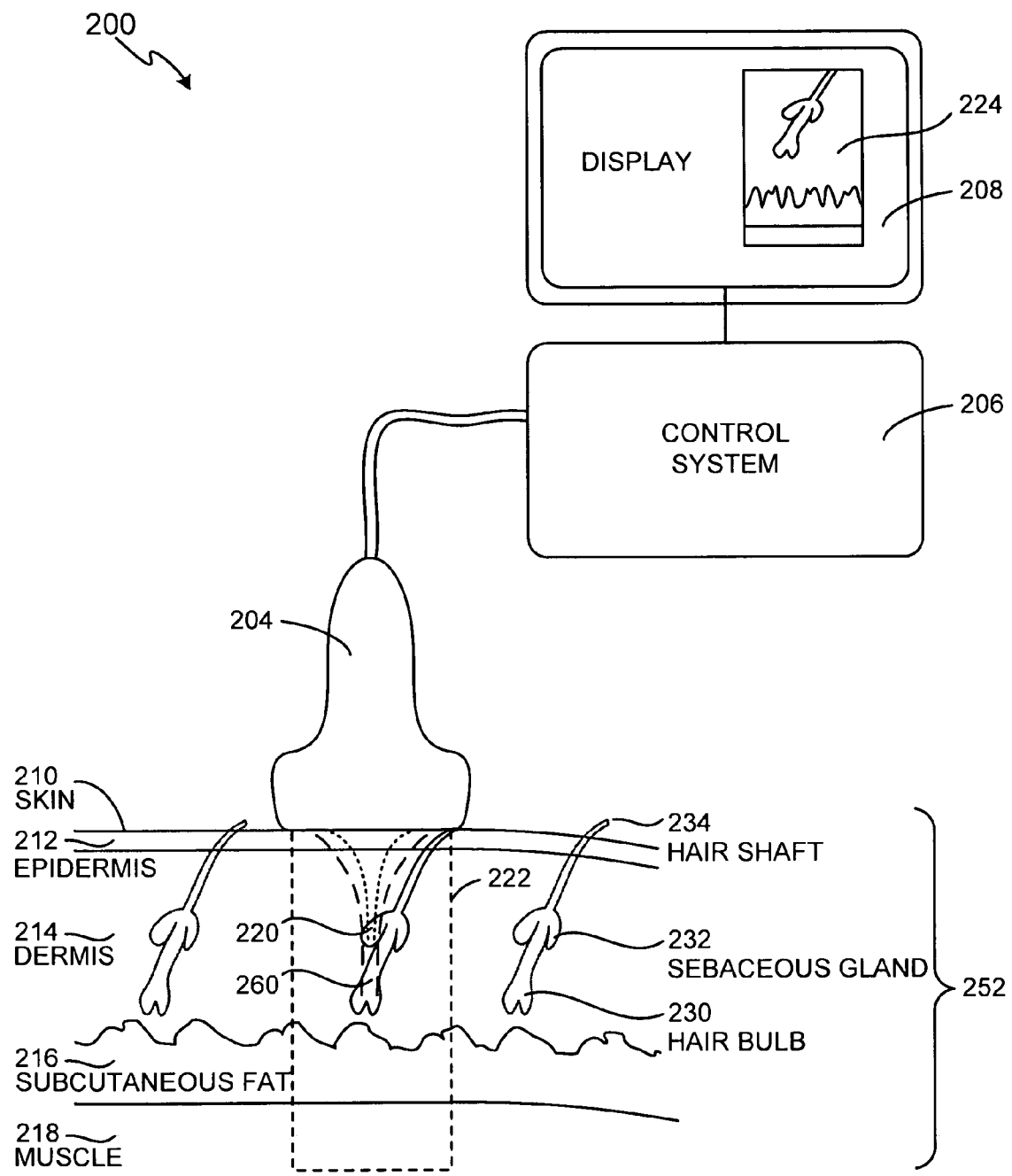

In accordance with another exemplary embodiment, with reference to FIG. 2E, a treatment system 200 can be configured for treatment over an expanded treatment region of interest 252 that includes a combination of tissues, such as subcutaneous fat/adipose tissue 216 and muscle 218, among others. A multiple of such tissues may be treated including sebaceous glands in combination with at least one of epidermis 212, dermis 214, adipose tissue 216, muscular fascia lying atop muscle tissue 218, mucous membrane, hair bulb 230, hair shaft 234, hair follicle between hair bulb 230 and epidermis 212, blood vessels, apocrine sweat glands, eccrine glands lying within dermis 214, fat 21 6 or muscle 218, and/or any other tissue of interest. For example, a treatment to region 220 of sebaceous gland 232 may be performed in combination with treatment to a region 260 of hair by suitable adjustment of the treatment spatial and/or temporal parameters of the transducers in probe 204.

Figure 3A:
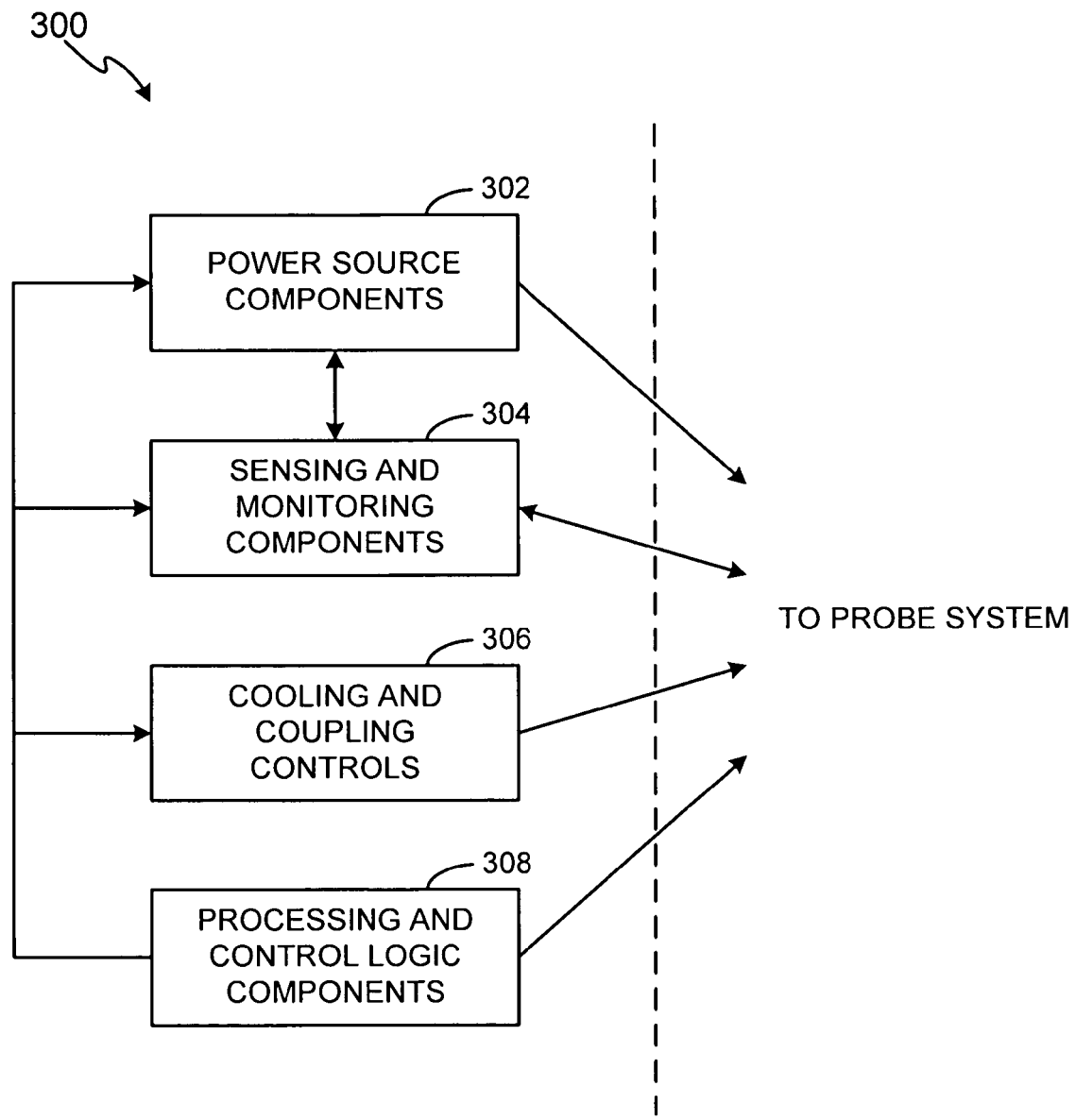
FIGS. 3A and 3B illustrate block diagrams of an exemplary control system in accordance with exemplary embodiments of the present invention.
Figure 3B:
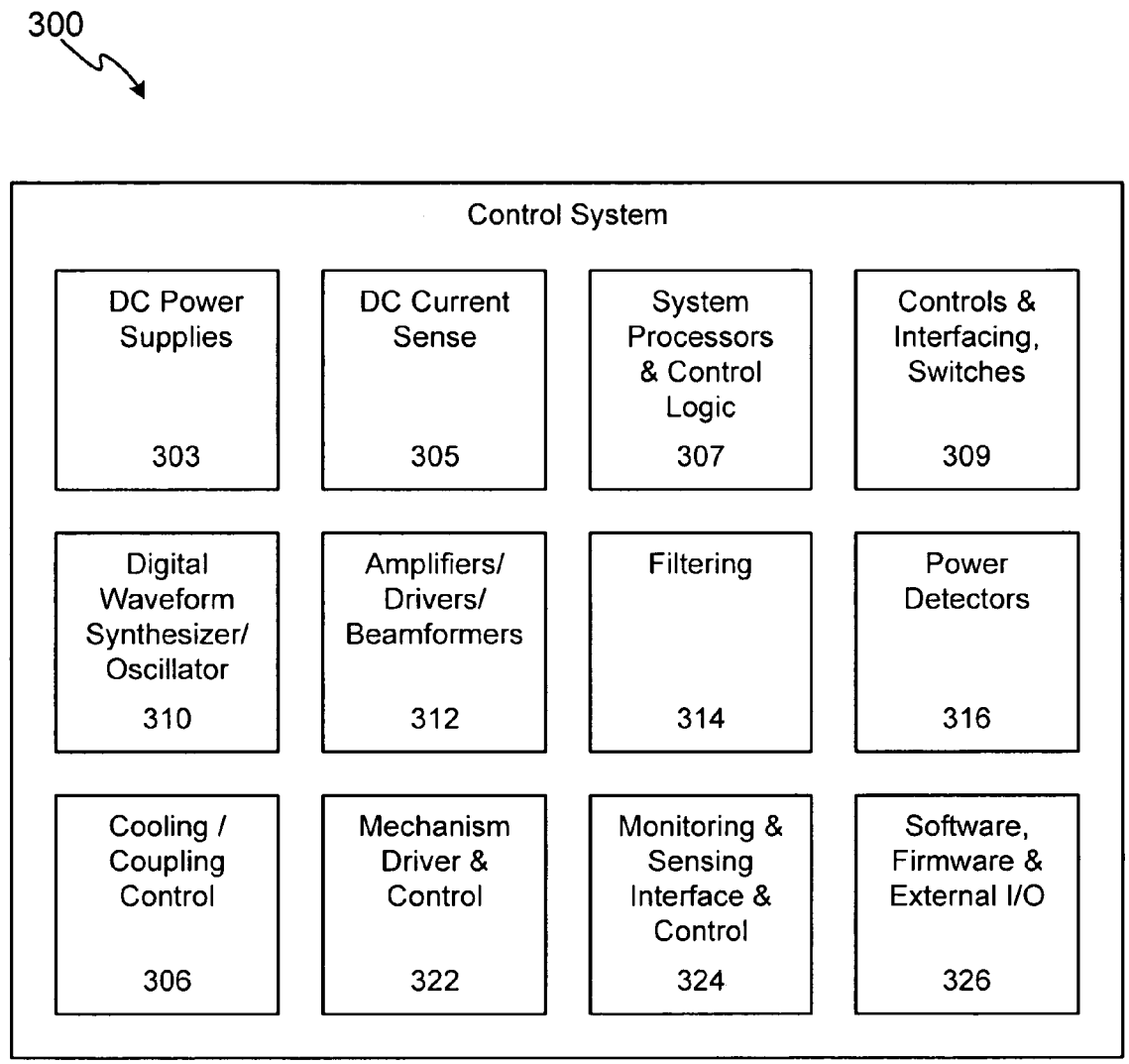

An exemplary control system 202 and display system 208 may be configured in various manners for controlling probe and system functionality for providing the various exemplary treatment methods illustrated above. For example, with reference to FIGS. 3A and 3B, in accordance with exemplary embodiments, an exemplary control system 300 can be configured for coordination and control of the entire therapeutic treatment process to achieve the desired therapeutic effect of thermal ablation to treat a sebaceous gland. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for controlled thermal injury of sebaceous glands, and the embodiments in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 204 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 200.

Cooling/coupling control systems 306 may be provided to remove waste heat from an exemplary probe 204, provide a controlled temperature at the superficial tissue interface and deeper into tissue, and/or provide acoustic coupling from transducer probe 204 to region-of-interest 206. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 204 can also be configured in various manners and comprise a number of reusable and/or disposable components and parts in various embodiments to facilitate its operation. For example, transducer probe 204 can be configured within any type of transducer probe housing or arrangement for facilitating the coupling of transducer to a tissue interface, with such housing comprising various shapes, contours and configurations. Transducer probe 204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 204 may also comprise cables and connectors; motion mechanisms, motion sensors and encoders; thermal monitoring sensors; and/or user control and status related switches, and indicators such as LEDs. For example, a motion mechanism in probe 204 may be used to controllably create multiple lesions, or sensing of probe motion itself may be used to controllably create multiple lesions and/or stop creation of lesions, e.g. for safety reasons if probe 204 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
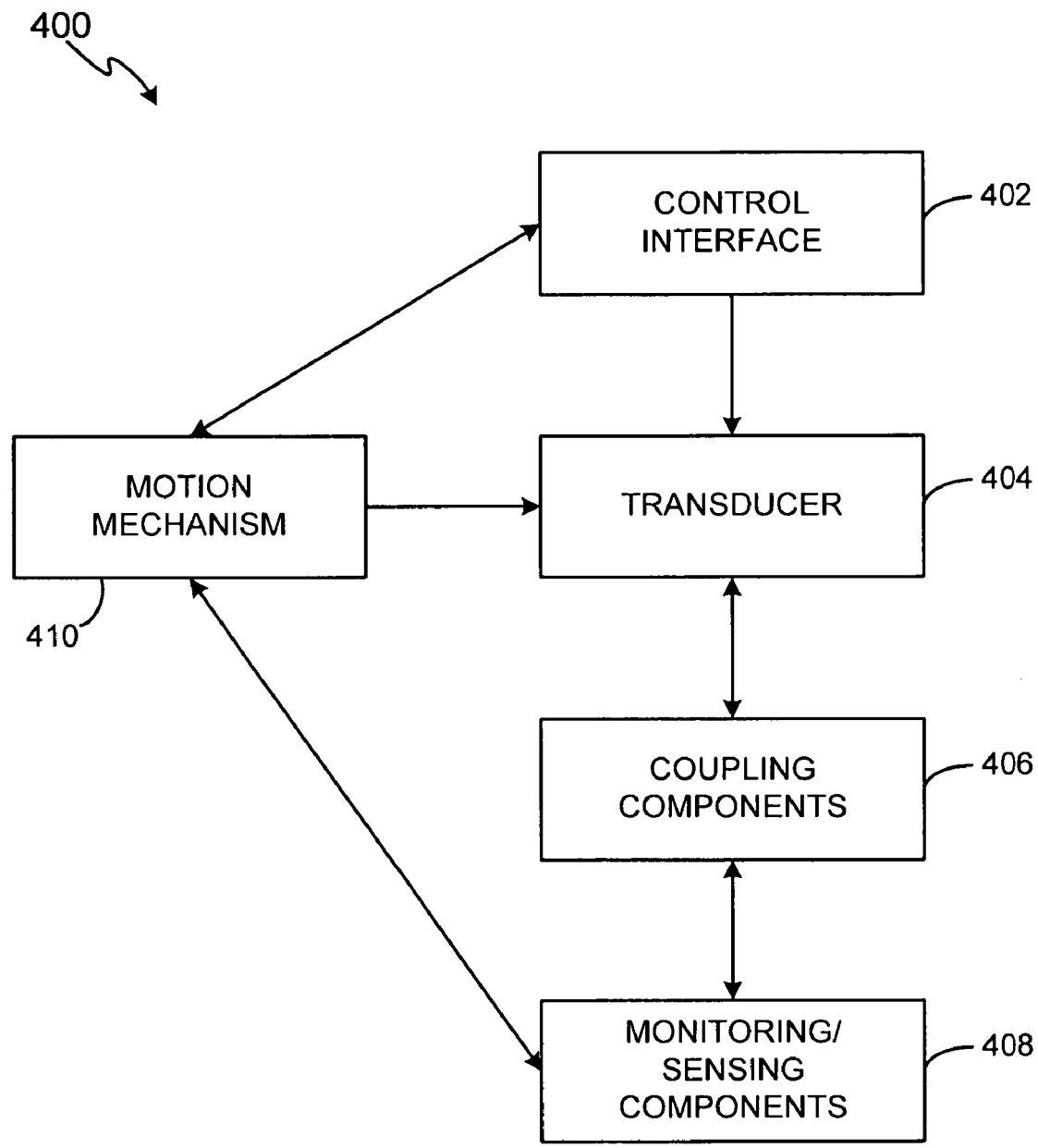
FIGS. 4A and 4B illustrate block diagrams of an exemplary probe system in accordance with exemplary embodiments of the present invention.
Figure 4B:
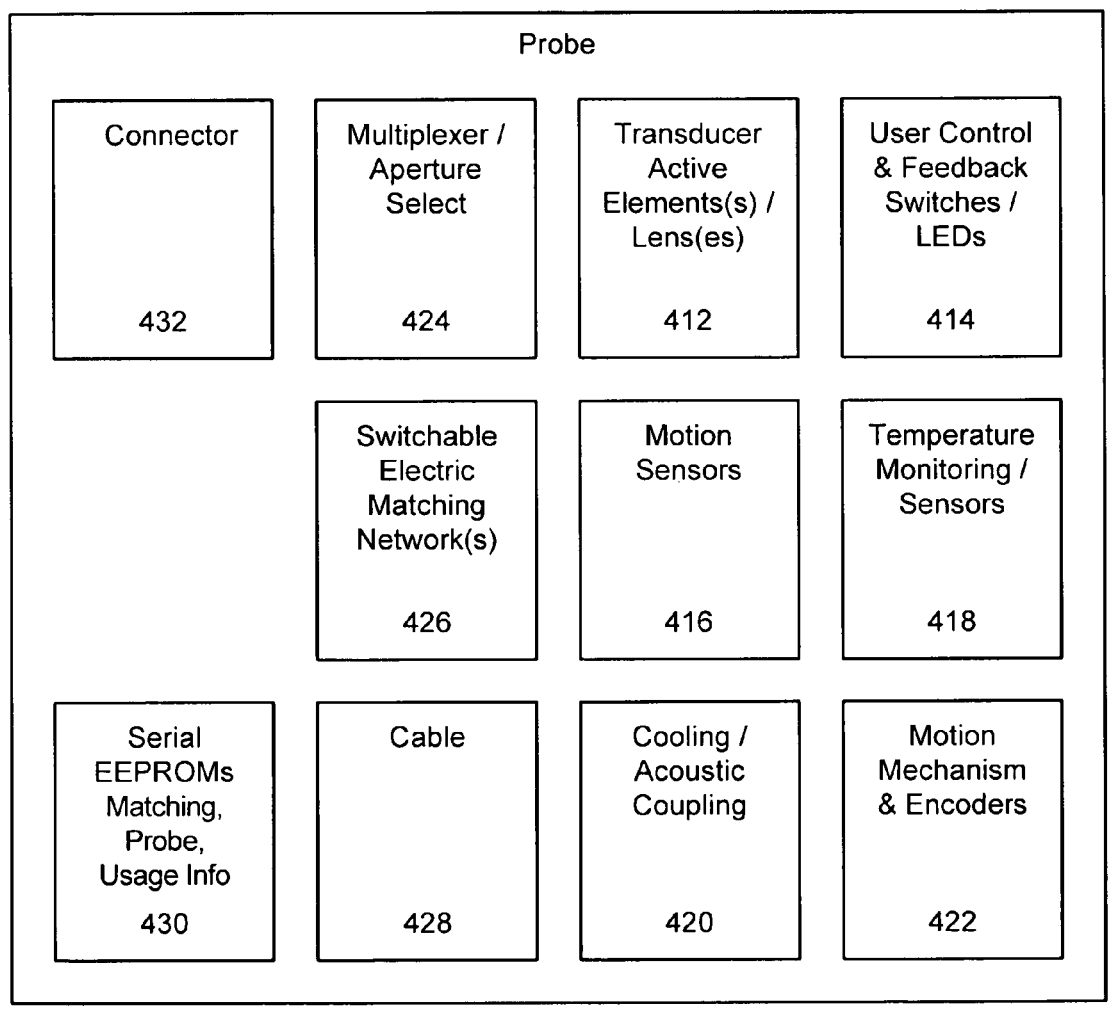

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide treatment of acne and sebaceous, and the embodiments in FIGS. 4A and 4B are merely for illustration purposes.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 41 2 and a region of interest. In addition to providing a coupling function, in accordance with an exemplary embodiment, coupling system 420 can also be configured for providing temperature control during the treatment application. For example, coupling system 420 can be configured for controlled cooling of an interface surface or region between transducer probe 400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 400.

Figure 11:
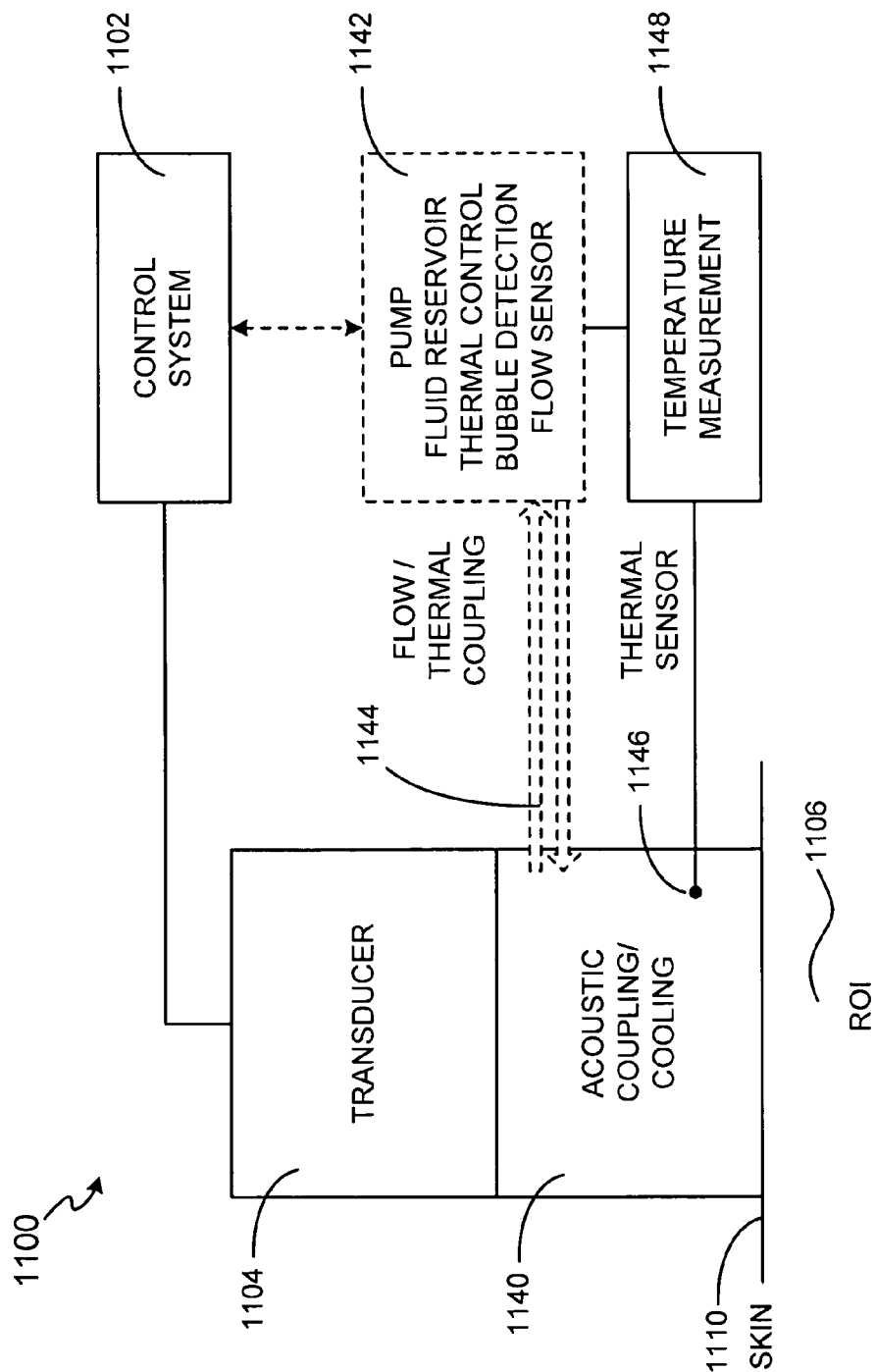
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1102, to provide thermal control at the probe to region-of-interest interface 1110 and deeper into tissue, and to remove potential waste heat from the transducer probe at region 1144. Temperature monitoring can be provided at the coupling interface via a thermal sensor 1146 to provide a mechanism of temperature measurement 1148 and control via control system 1106 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

With continued reference to FIG. 4, monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism 422 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for treating of acne and sebaceous glands and targeted regions. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of approximately 2 kHz to 75 MHz, such as for imaging applications. Transduction element 412 can also be configured with a second thickness selected to provide a center operating frequency of approximately 2 to 50 MHz, and typically between 2 MHz and 25 MHz for therapy application. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range.

Figure 5:
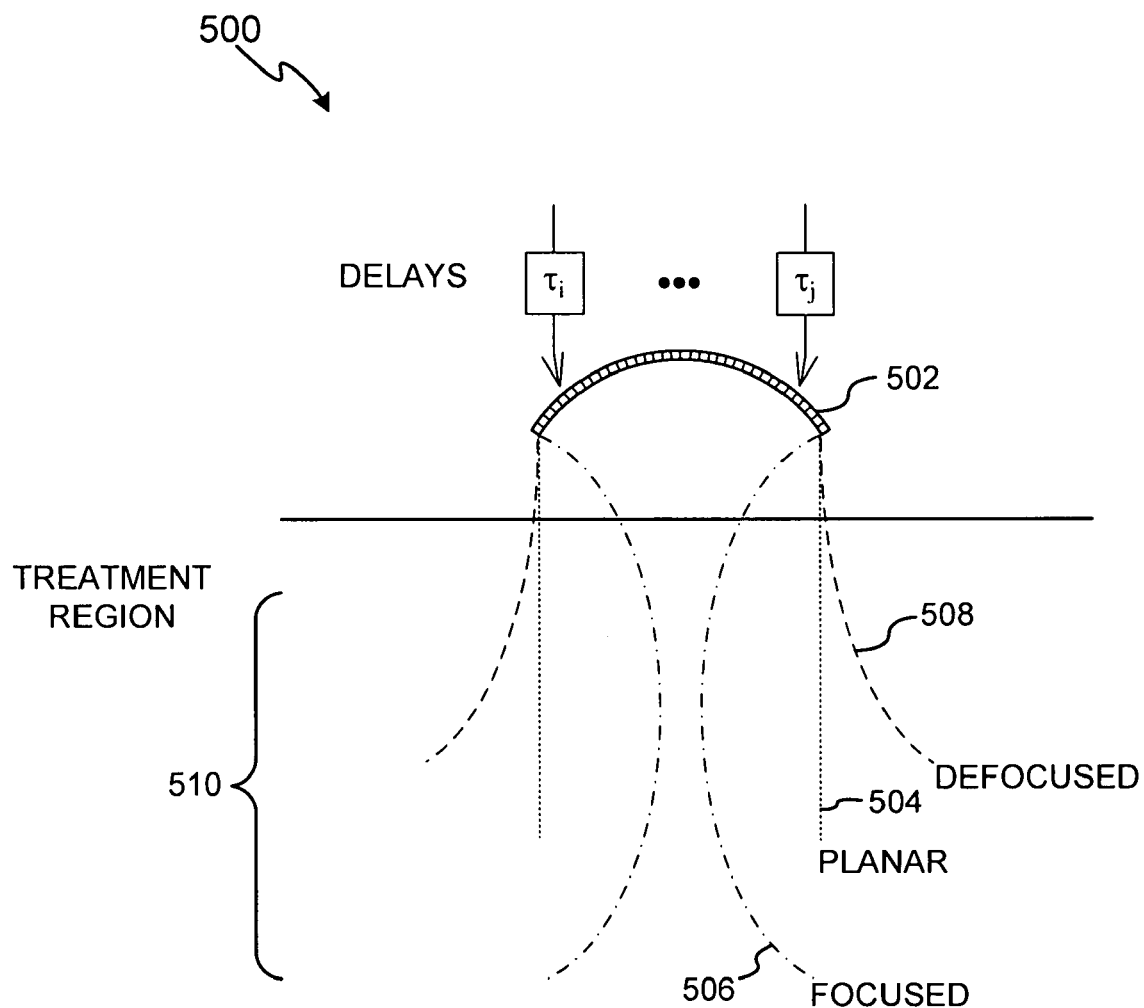
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944,499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 6A and 6B, transducer 600 may also be configured with an electronic focusing array 604 in combination with one or more transduction elements 606 to facilitate increased flexibility in treating ROI 610. Array 604 may be configured in a manner similar to transducer 502. That is, array 604 can be configured as an array of electronic apertures that may be operated by a variety of phases via variable electronic time delays, for example, $T_1, T_2 \ldots T_j$. By the term "operated," the electronic apertures of array 604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606A are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
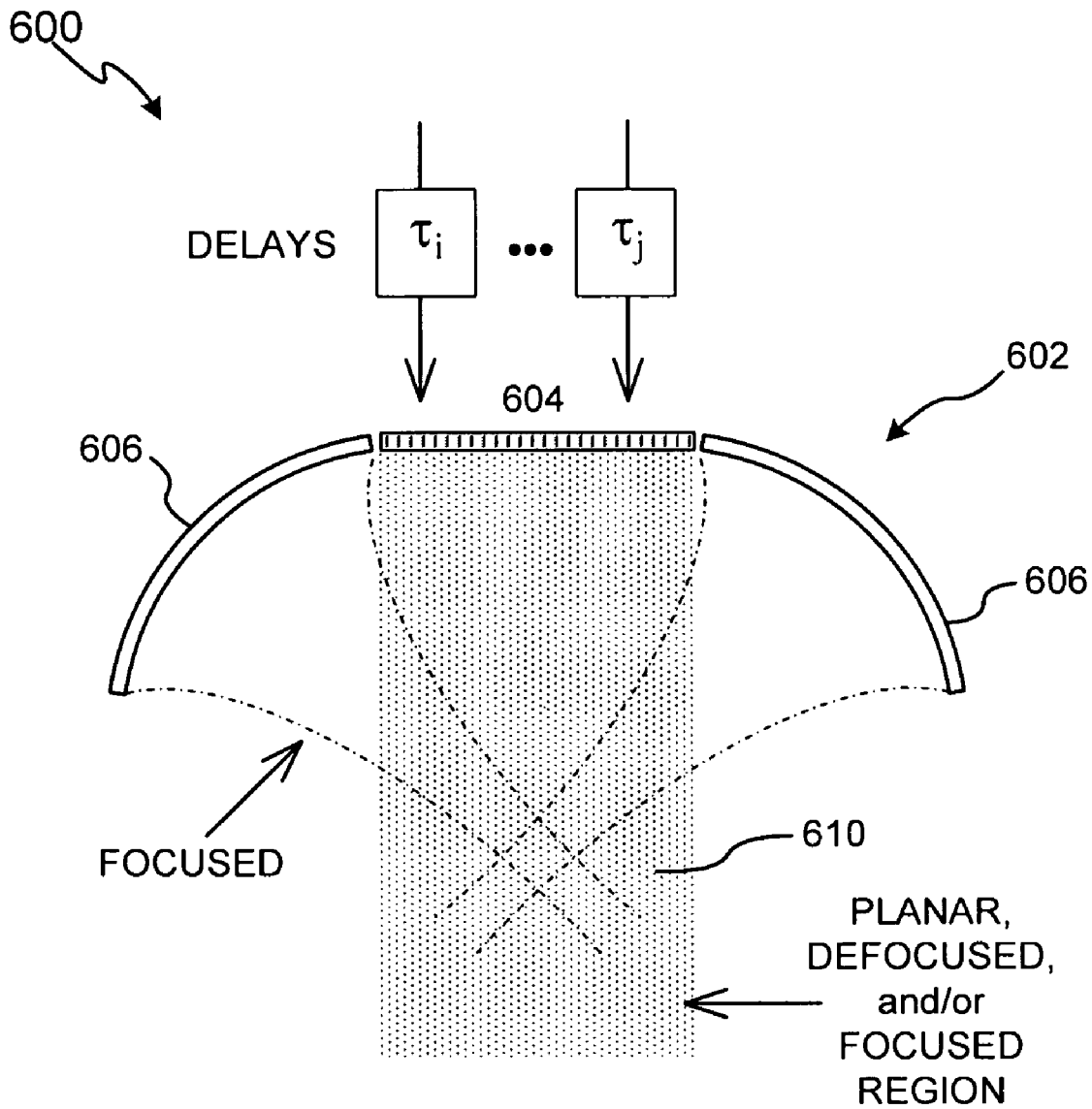
FIGS. 6A and 6B illustrate cross-sectional diagrams of an exemplary transducer in accordance with exemplary embodiments of the present invention.
Figure 6B:
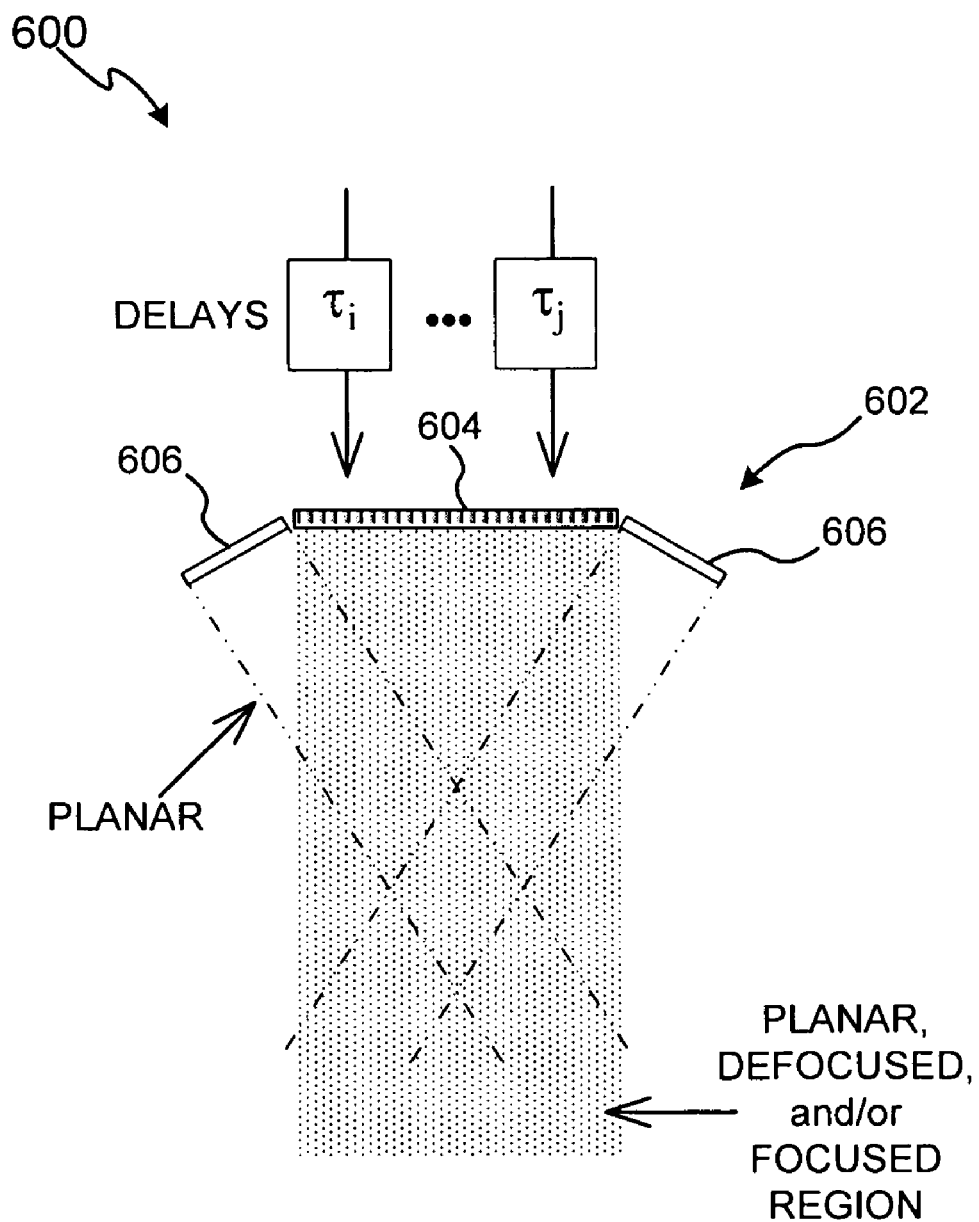

In another exemplary embodiment, depicted in FIG. 6B, transduction elements 606[B] can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 9:
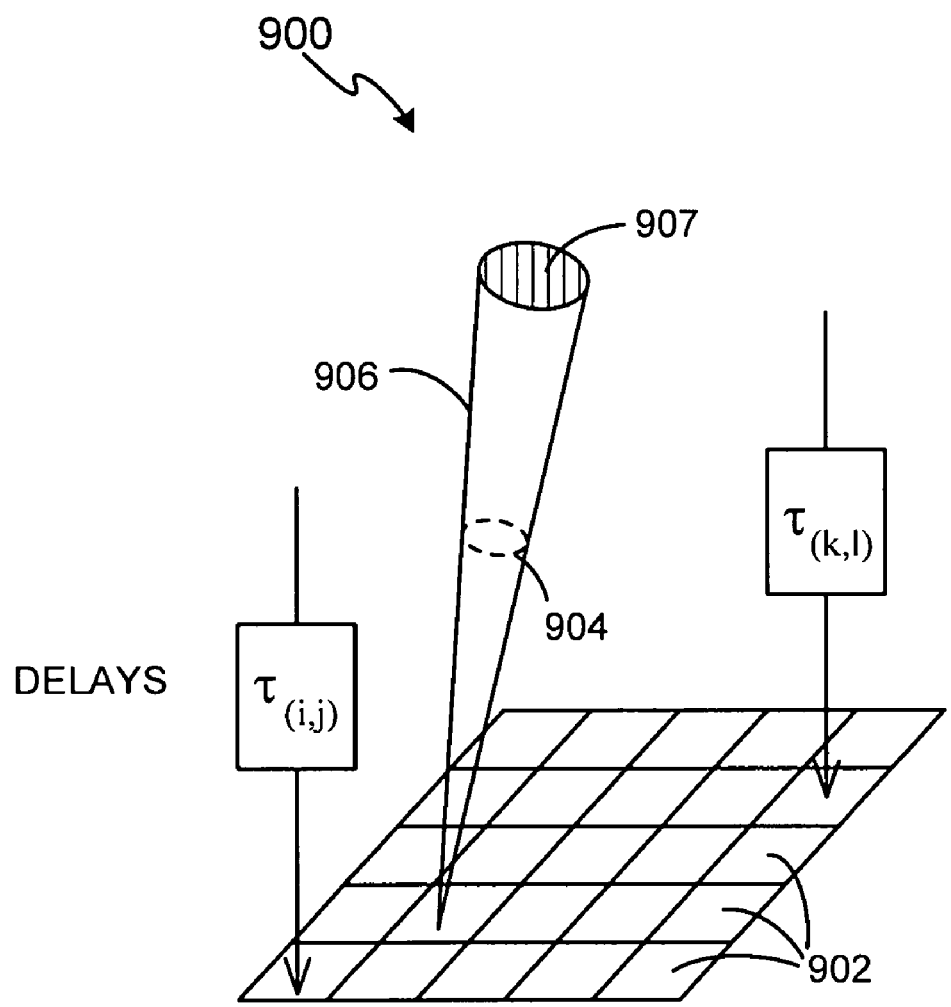
FIG. 9 illustrates an exemplary transducer configured as a two-dimensional array for ultrasound treatment in accordance with an exemplary embodiment of the present invention.

In accordance with another exemplary embodiment, transducer 404 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

Figure 8A:
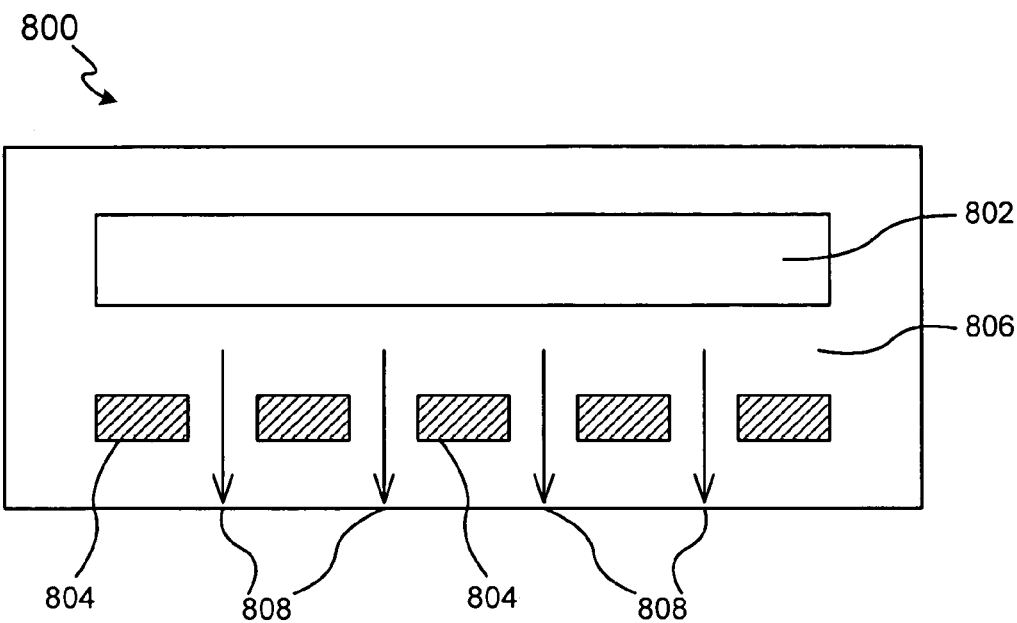
FIGS. 8A and 8B illustrate cross-sectional diagrams of an exemplary transducer in accordance with another exemplary embodiment of the present invention.
Figure 8B:
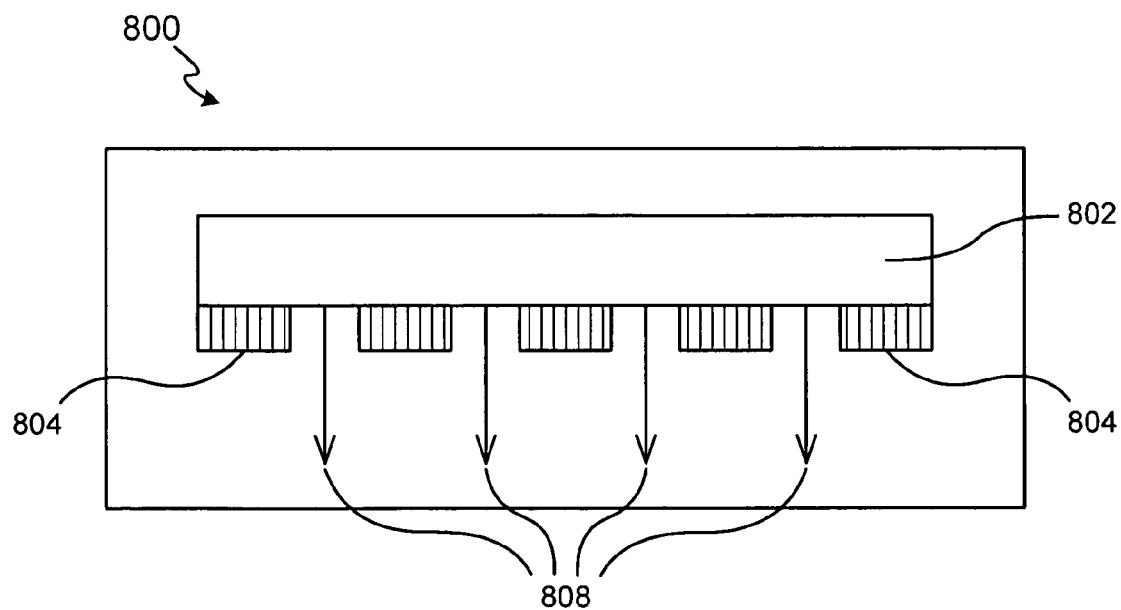

With reference to FIGS. 8A and 8B, transducer 404 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
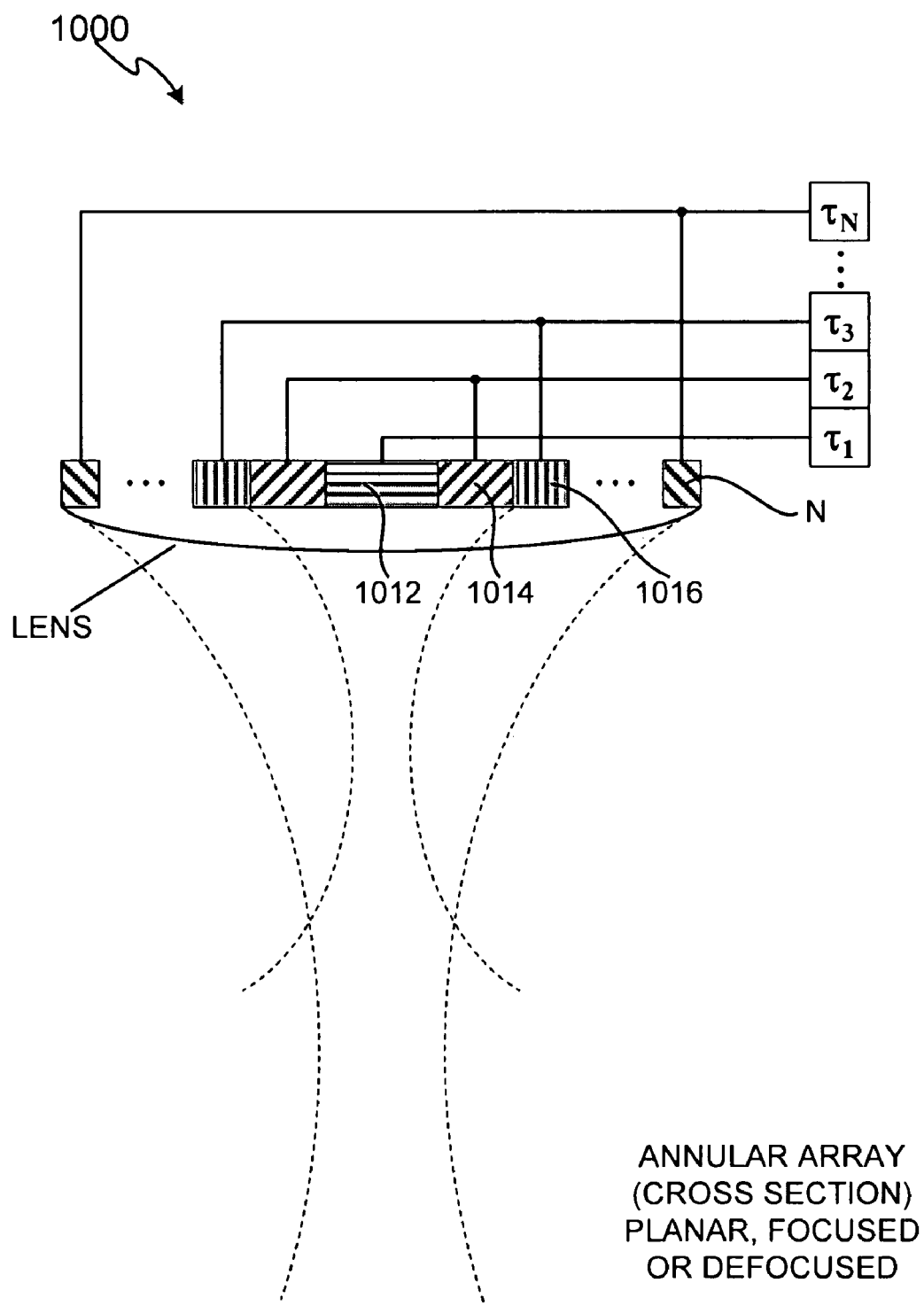
FIGS. 10A-10F illustrate cross-sectional diagrams of exemplary transducers in accordance with other exemplary embodiments of the present invention.
Figure 10B:
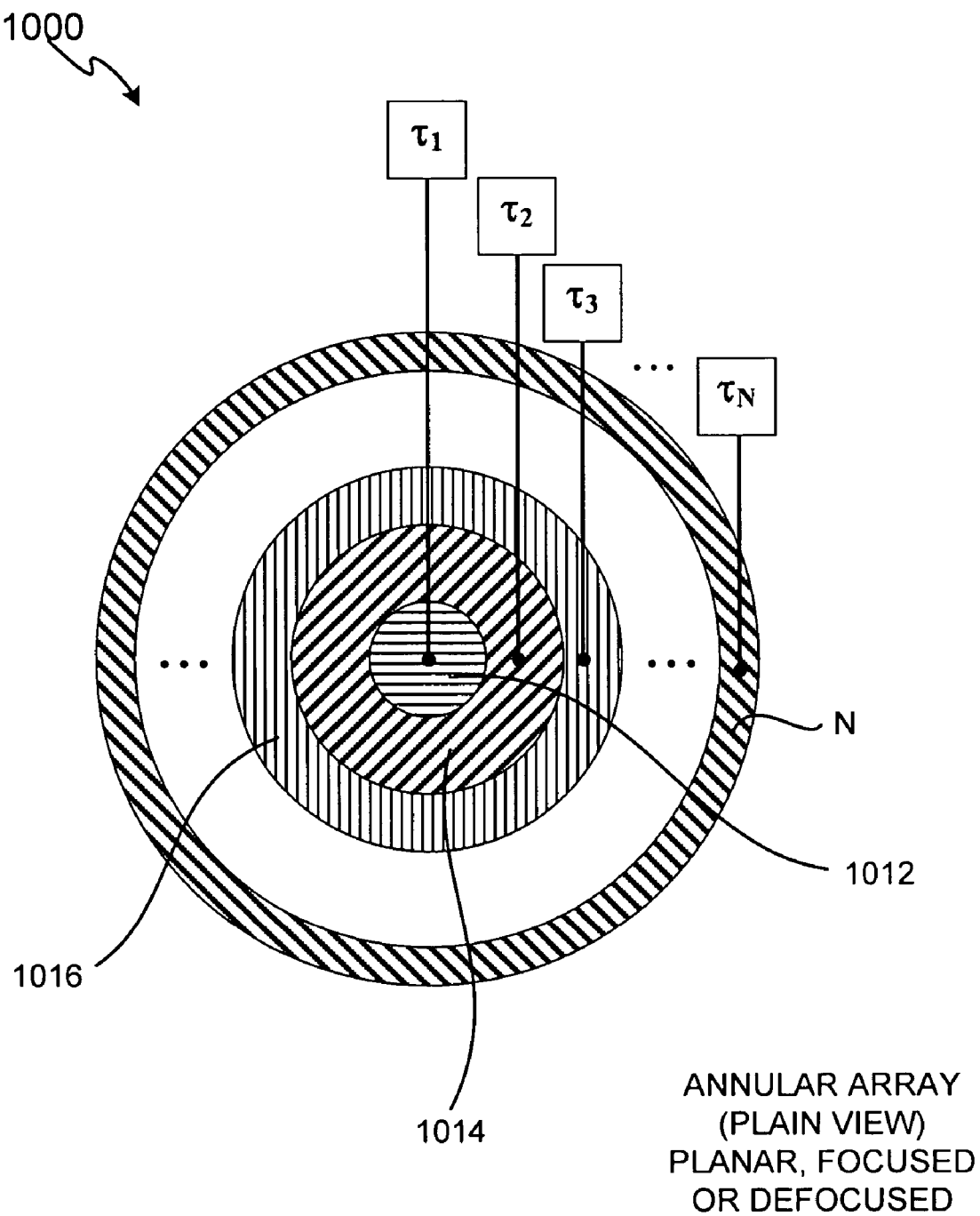
Figure 10C:
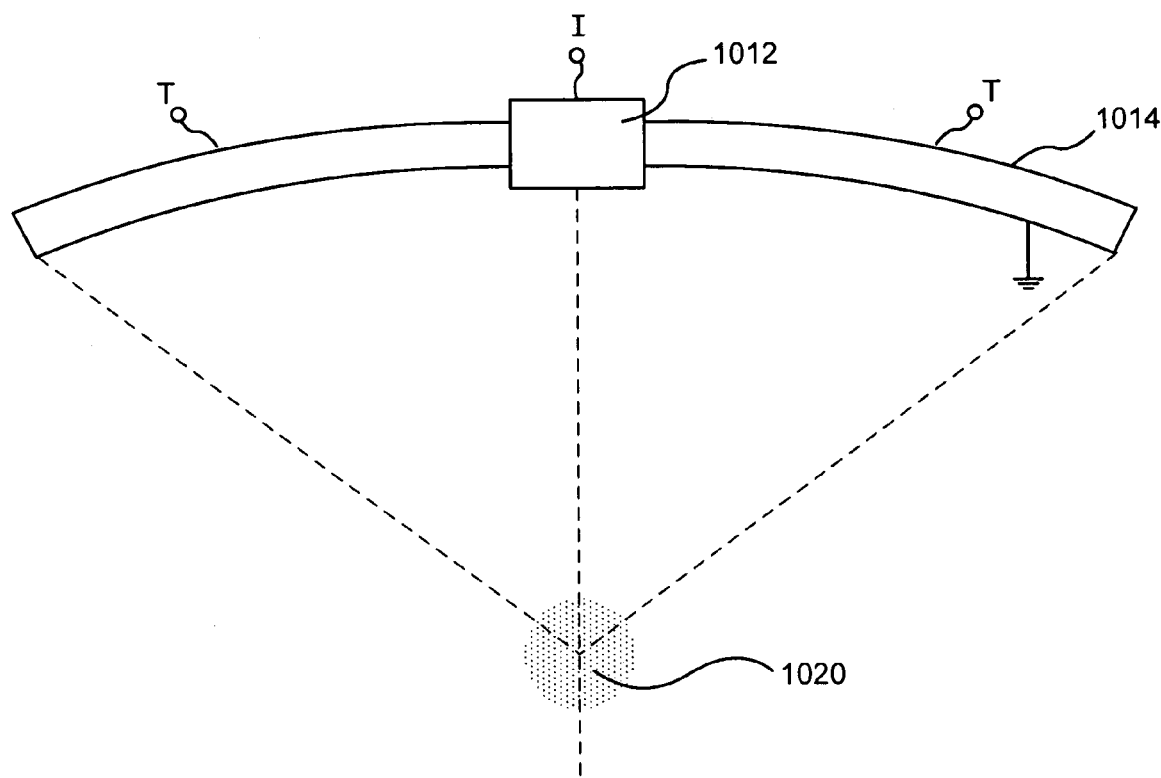
Figure 10D:
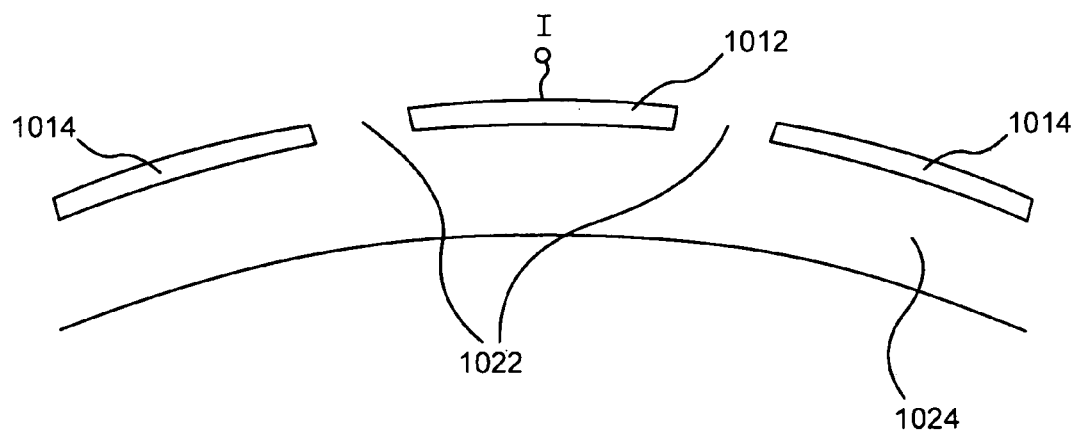
Figure 10E:
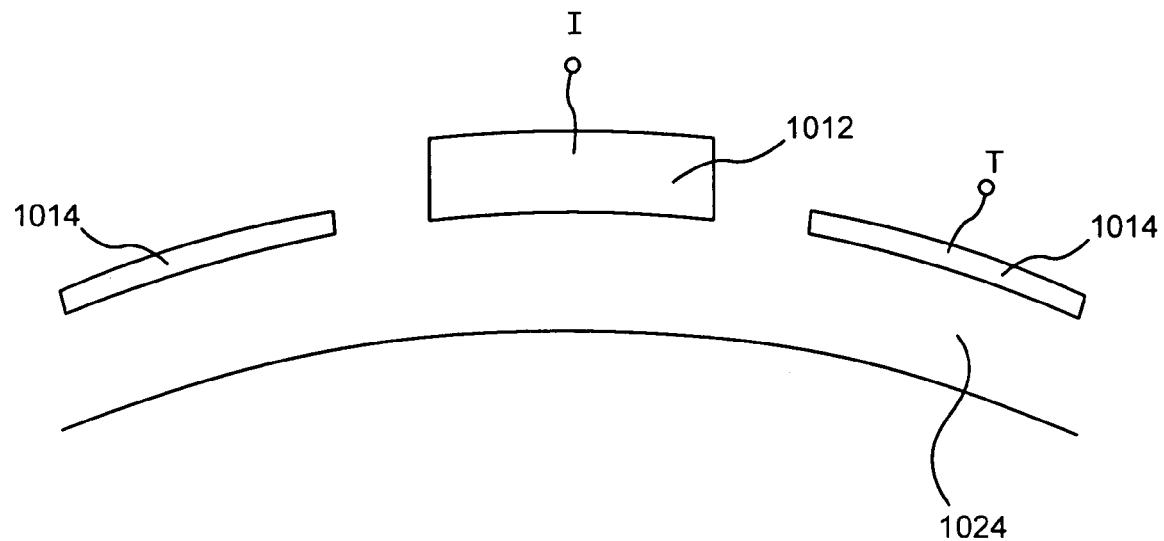

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $T_1, T_2, T_3 \ldots T_N$. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 800 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with various exemplary embodiments of the present invention, transducer 404 may be configured to provide one, two and/or three-dimensional treatment applications for focusing acoustic energy to one or more regions of interest. For example, as discussed above, transducer 404 can be suitably diced to form a one-dimensional array, e.g., transducer 602 comprising a single array of sub-transduction elements.

In accordance with another exemplary embodiment, transducer 404 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer 404 may be suitably configured to provide three-dimensional treatment. For example, to provide three dimensional treatment of a region of interest, with reference again to FIG. 1, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

In accordance with other exemplary embodiments, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
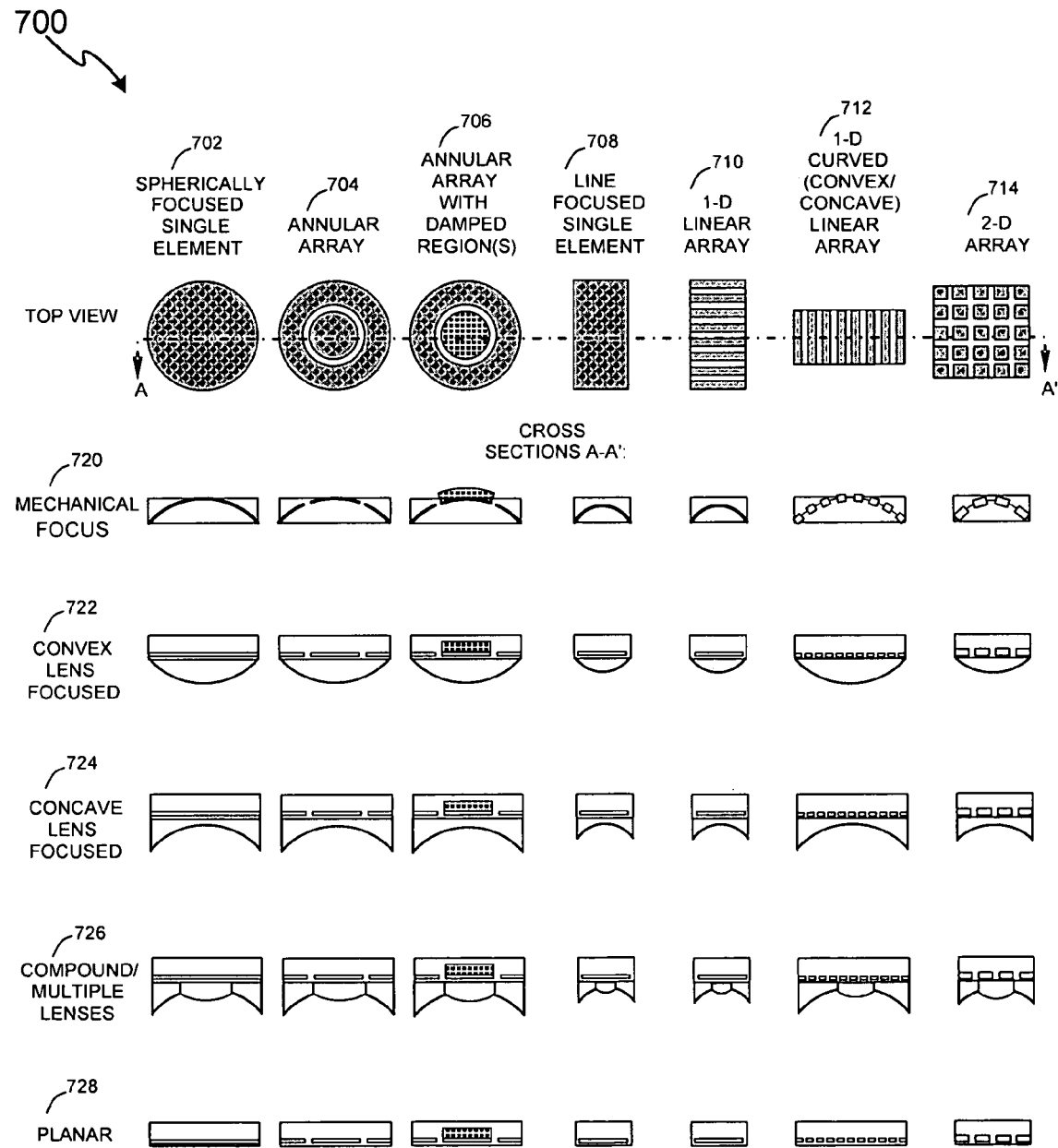
FIG. 7 illustrates exemplary transducer configurations for ultrasound treatment in accordance with various exemplary embodiments of the present invention.
Figure 10F:
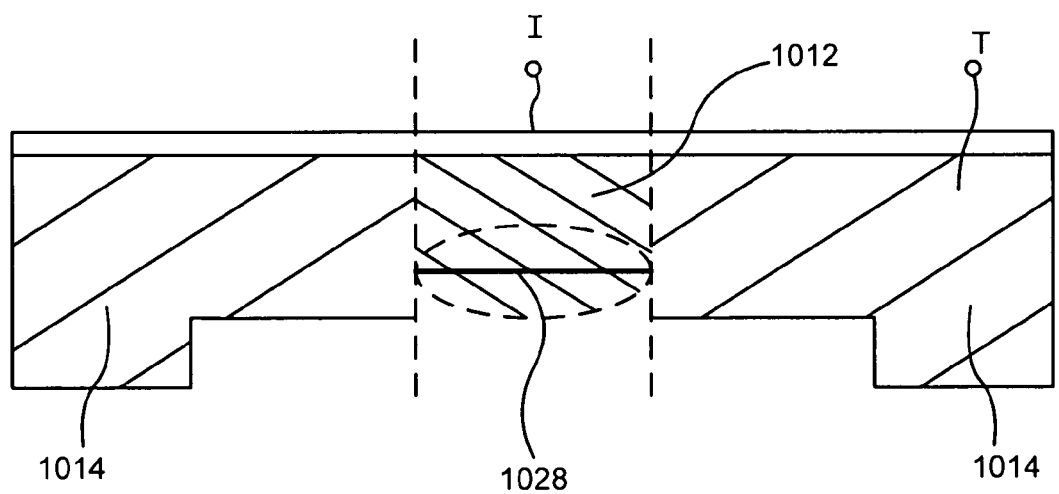

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays in concave or convex form, with or without elevation focusing, 2-D arrays, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 10C-10F.

Moreover, such transduction elements 700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 700 may also comprise one or more matching layers configured along with the piezoelectrically active material. In addition to or instead of piezoelectrically active material, transduction elements 700 can comprise any other materials configured for generating radiation and/or acoustical energy. A means of transferring energy to and from the transducer to the region of interest is provided.

Figure 12:
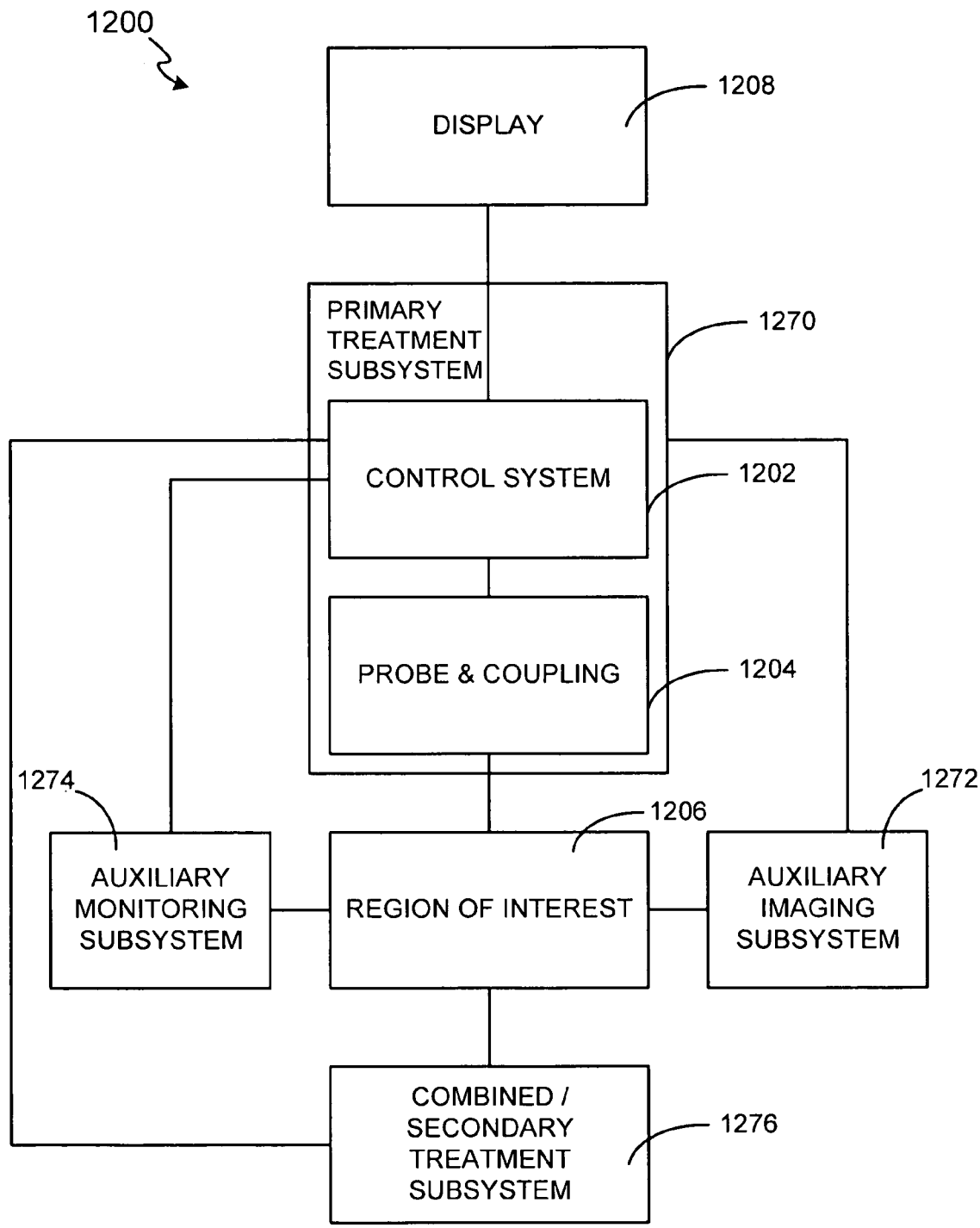
FIG. 12 illustrates a block diagram of an ultrasound treatment system combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treatment of acne and sebaceous glands can further comprise an auxiliary imaging modality 1272 and/or auxiliary monitoring modality 1274 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of the region-of-interest, including imaging/monitoring enhancements. Such imaging/monitoring enhancement for ultrasound imaging via probe 1204 and control system 1202 can comprise M-mode, persistence, filtering, color, Doppler, and harmonic imaging among others; furthermore an ultrasound treatment system 1270, as a primary source of treatment, may be combined with a secondary source of treatment 1276, including radio frequency (RF), intense pulsed light (IPL), laser, infrared laser, microwave, or any other suitable energy source.

Figure 13:
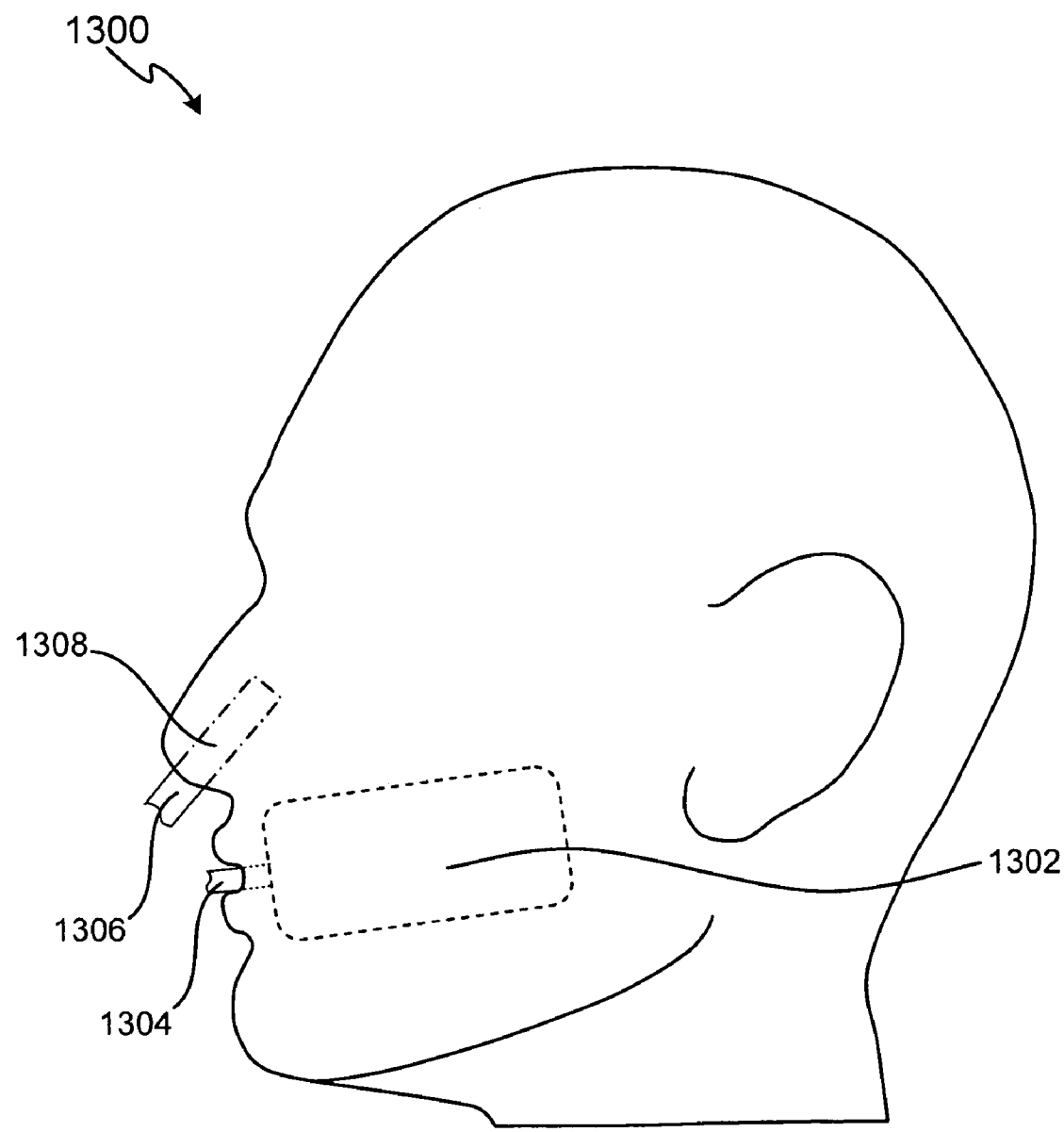
FIG. 13 illustrates a schematic diagram with imaging, therapy, or monitoring being provided with one or more active or passive oral inserts in accordance with an exemplary embodiment of the present invention.

In accordance with another exemplary embodiment, with reference to FIG. 13, treatment composed of imaging, monitoring, and/or therapy to a region of interest 1302 and/or 1308 may be aided, augmented, and/or delivered with passive or active devices 1304 and/or 1306 within the oral and/or nasal cavity, respectively. For example, if passive or active device 1304 and/or 1306 are second transducers or acoustic reflectors acoustically coupled to the mucous membranes it is possible to obtain through transmission, tomographic, or round-trip acoustic waves which are useful for treatment monitoring, such as in measuring acoustic speed of sound and attenuation, which are temperature dependent; furthermore such transducers could be used to treat and/or image. In addition an active, passive, or active/passive object 1304 and/or 1306 may be used to flatten the skin, and/or may be used as an imaging grid, marker, or beacon, to aid determination of position. A passive or active device 1304 and/or 1306 may also be used to aid cooling or temperature control. Natural air in the oral cavity and/or nasal cavity may also be used as passive device 1304 and/or 1306 whereby it may be utilized to as an acoustic reflector to aid thickness measurement and monitoring function.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

What is claimed is:

1. A method for providing treatment of acne and sebaceous glands, said method comprising:
   localizing at least one targeted region within a region of interest, said localizing configured for identifying at least one sebaceous gland;
   targeting delivery of ablative ultrasound energy from a transducer probe to said at least one sebaceous gland at a depth of about 1 to about 7 mm; and
   monitoring results of said targeted delivery within said at least one sebaceous gland during and after said targeted delivery to continue planning of treatment.

2. The method of claim 1, wherein said localizing at least one targeted region comprises imaging a region of interest to identify said at least one sebaceous gland.

3. The method of claim 1, said targeting of delivery of ablative ultrasound energy comprises destroying the function of said sebaceous gland within a specified treatment depth identified through localization of said sebaceous gland.

4. The method of claim 1, wherein said targeting of delivery of ablative ultrasound comprises adjustable control of spatial parameters and temporal parameters of said transducer probe to generate conformal lesions of specifically targeted shapes, sizes and orientations.

5. The method of claim 1, wherein said targeting delivery of ablative ultrasound comprises producing said treatment regions in spatially defined patterns to facilitate healing of tissue.

6. The method according to claim 5, wherein said producing said treatment regions in spatially defined patterns comprises producing a discrete locus of spaced lesions comprising at least one of cross-stitch, cigar-shaped, or wedge-shaped lesions.

7. The method of claim 1, wherein said monitoring results comprises measurement of results of treatment of said at least one sebaceous gland as visualized during and after said target delivery of ablative ultrasound.

8. The method of claim 1, wherein said monitoring results comprises monitoring the temperature profile of said targeted region.

9. The method of claim 1, wherein said targeted of delivery of ablative ultrasound comprises producing of a matrix of spaced treatment spots comprising at least one of two-dimensional and three-dimensional matrix of lesions along a scanned pattern created by scanning of said transducer probe.

10. The method according to claim 5, wherein said producing said treatment regions in spatially defined patterns comprises producing a discrete locus of spaced conformal lesions based on control of spatial and temporal parameters.

11. The method according to claim 1, wherein said localizing at least one targeted region comprises generating three-dimensional imaging information and said targeting comprises treating three-dimensional treatment region.

12. The method according to claim 1, wherein said targeting of delivery further comprises cooling through any tissue regions between and including skin and said at least one sebaceous gland to facilitate treatment.

13. A method for providing treatment of acne and sebaceous glands, said method comprising:
   localizing at least one targeted region for identifying at least one sebaceous gland;
   targeting delivery of ablative ultrasound energy from a transducer probe to said at least one sebaceous gland at a specified treatment depth of about 1 to about 7 mm for destroying any function of said at least one sebaceous gland within said specified treatment depth, wherein said targeting of delivery comprises delivery of ablative ultrasound energy in spatially defined patterns producing a discrete locus of spaced lesions comprising at least one of a cross-stitch, a cigar-shaped, and a wedge-shaped lesion; and monitoring results of said targeted delivery within said at least one sebaceous gland during and after said targeted delivery to continue planning of treatment.

14. The method of claim 13, further comprising producing spatially defined patterns in said at least one targeted region to facilitate healing of tissue.

15. The method according to claim 14, wherein said producing said spatially defined patterns in said at least one targeted region further comprises producing a discrete locus of spaced conformal lesions based on control of spatial and temporal parameters.

16. The method according to claim 13, further comprising generating three-dimensional imaging information of said least one sebaceous gland.

17. The method according to claim 16, further comprising treating a three-dimensional treatment region as defined by said three-dimensional imaging information of said least one sebaceous gland.

18. A method of providing a treatment for acne by a reduction in function of pilosebaceous glands, the method comprising:

imaging a treatment area below a skin surface, said treatment area comprising at least portion of said pilosebaceous gland;

identifying at least portion of said pilosebaceous gland in said treatment area;

delivering ultrasound energy to said at least portion of said pilosebaceous gland;

coagulating said least a portion of said pilosebaceous gland; and monitoring said pilosebaceous gland for a reduction in function; thereby reducing an appearance of acne on said skin surface.

19. The method of claim 18 further comprising producing spatially defined patterns in said treatment area to facilitate healing of tissue.

20. The method according to claim 19, wherein said producing spatially defined patterns in said treatment area comprises producing a discrete locus of spaced conformal lesions based on control of spatial and temporal parameters.

21. The method according to claim 19, wherein said producing spatially defined patterns in said treatment area comprises producing a discrete locus of spaced lesions comprising at least one of cross-stitch, cigar-shaped, or wedge-shaped lesions.

22. The method of claim 18, wherein said delivering ultrasound energy to said at least portion of said pilosebaceous gland further comprises adjustably controlling of spatial parameters and temporal parameters of a transducer probe to generate conformal lesions of specifically targeted shapes, sizes and orientations.

23. The method of claim 18, further comprising producing of a matrix of spaced treatment spots comprising at least one of two-dimensional and three-dimensional matrix of lesions.

24. The method according to claim 18, further comprising generating three-dimensional imaging information comprising generating three-dimensional imaging information of said least one sebaceous gland.

25. The method according to claim 18 further comprising treating a three-dimensional treatment region as defined by said three-dimensional imaging information of said least one sebaceous gland.

* * * * *